United States Patent [19]
Roseman et al.

[11] Patent Number: 5,792,647
[45] Date of Patent: Aug. 11, 1998

[54] BACTERIAL CATABOLISM OF CHITIN

[75] Inventors: Saul Roseman, Baltimore, Md.; Bonnie Bassler, Princeton, N.J.; Nemat O. Keyhani, Baltimore, Md.; Edith Chitlaru, Rehovot, Israel; Chris Rowe, Timonium; Charles Yu, Lutherville, both of Md.

[73] Assignee: The Johns Hopkins University, Baltimore, Md.

[21] Appl. No.: 386,727

[22] Filed: Feb. 13, 1995

[51] Int. Cl.$^6$ .............................. C12N 15/56; C12N 9/42; C12N 1/21
[52] U.S. Cl. .................. 435/252.3; 536/23.2; 435/172.3; 435/320.1; 435/209; 435/712; 435/909
[58] Field of Search ....................... 536/23.2; 435/252.3, 435/172.3, 209, 320.1, 71.2, 909

[56] References Cited

PUBLICATIONS

Bassler et al., "Chitin utilization by marine bacteria", The Journal of Biological Chemistry, Dec. 25, 1991, vol. 266, No. 36, pp. 24276–22486.
C. Yu et al., "Chitin Utilization by Marine Bacteria: A Physiological Function for Bacterial Adhesion to Immobilized Carbohydrates"; J. Biol. Chem., vol. 266, No. 36, (1991) pp. 24260–24667.
B. Bassler et al., "Chitin Utilization by Marine Bacteria: Chemotaxis to Chitin Oligosaccharides by Vibrio Furnissii"; J. Biol. Chem., vol. 266, No. 36, (1991) pp. 24268–24275.
B. Bassler et al., "Chitin Utilization by Marine Bacteria: Degradation and Catabolism of Chitin Oligosaccharides by Vibrio Furnissii"; J. Biol. Chem., vol. 266, No. 36, (1991) pp. 24276–24286.

C. Yu et al., "Chemotaxis of the Marine Bacterium Vibrio Funissii to Sugars: A Potential Mechanism for Initiating the Chitin Catabolic Cascade"; J. Biol. Chem., vol. 268, No. 13, (1993) pp. 9405–9409.

C. Yu et al., "The Sugar–Specific Adhesion/Deadhesion Apparatus of the Marine Bacterium. . ."; Biochemical and Biophysical Research Communications, vol. 149, No. 1, (1987) pp. 86–92.

B. Bassler et al., "Chemotaxis to Chitin Oligosaccharides by Vibrio Furnissii, A Chitinivorous Marine Bacterium"; Biochemical Biophysical Research Communications, vol. 161, No. 3, (1989) pp. 1172–1176.

P. Lerouge, "Symbiotic Host Specificty between Leguminous Plants and Rhizobia is Determined by Substituted and Acylated. . ."; Centre Regional de Spectroscopie, URA–CNRS 464, Universite de Rouen 76821, pp. 127–134.

Primary Examiner—Rebecca E. Prouty
Attorney, Agent, or Firm—Fish & Richardson, P.C.

[57] ABSTRACT

The present invention reveals the cloning of four genes involved in the catabolism of chitin in Vibrio furnissii: endI encodes periplasmic chitodextrinase, exoI encodes periplasmic β-N-acetylglucosaminidase, exoII encodes aryl β-N-acetyl-glucosaminidase and chiA encodes extracellular chitinase. The complete nucleotide sequence for each of the four genes and the complete amino acid for the corresponding enzymes are demonstrated along with host cells capable of expressing the recombinant enzymes. The present invention also describes four specific strains of V. furnissii having deletions in genes involved in the catabolic pathway of chitin and a process for the production of chitin oligosaccharides.

4 Claims, 7 Drawing Sheets

5,792,647

BACTERIAL CATABOLISM OF CHITIN

This patent application was supported in part by grants N0014-91-J-4033, N00014-92-J-1936 and N00014-93-1-0630 from the Office of Naval Research and grant 5 R37 GM38759 from the National Institutes of Health. The Government has certain rights in the invention.

BACKGROUND OF THE INVENTION

1. Field of the Invention

A. The present invention relates to the isolation and characterization of genes involved in the catabolic pathway of chitin in *Vibrio furnissii*. More specifically, the present invention relates to the cloning of genes for four β-N-acetylglucosaminidases, two endo- and two exoenzymes:

chiA encodes an endoenzyme, extracellular chitinase or E-chitinase, endI encodes an endoenzyme, periplasmic chitodextrinase, or Endo-I, exoI encodes an exoenzyme, periplasmic β-N-acetylglucosaminidase or Exo-I and exoII encodes an exoenzyme, an aryl β-N-acetylglucosaminidase, or Exo-II.

The functions of these enzymes in the chitin catabolic pathway are schematically illustrated in FIG. 1. An endoenzyme is defined as an enzyme that cleaves internal bonds in its macromolecular substrate. In the case of glycosidases that hydrolyze glycosidic bonds in polysaccharides, an endoenzyme hydrolyzes internal glycosidic bonds. A chitinase is an example of an endoenzyme. An exoenzyme is defined as an enzyme that progressively hydrolyzes the terminal units of macromolecular substrates. In the case of glycosidases, the exo-glycosidases are exoenzymes that hydrolyze the terminal (non-reducing) end of the polysaccharide chain.

B. The transformation of host cells with the cloned genes and the isolation and characterization of the recombinant enzymes are also detailed.

C. The cloned genes are used to create four strains of *V. furnissii* having specific deletion mutations.

D. The enzymes, cloned genes and deletion mutants are used in a novel method for producing chitin oligosaccharides.

Chitin is the second most abundant organic substance in nature and is a homopolymer of $\beta,1\rightarrow4$ N-acetylglucosamine residues. Approximately $10^{11}$ metric tons are produced annually in the aquatic biosphere alone. These huge quantities of highly insoluble polysaccharide represent a potential devastating threat to the environment. The oceans would be depleted of carbon and nitrogen in a matter of decades and the respective cycles would cease if chitin was not converted to a biologically useful form. In fact, marine sediments contain only traces of chitin. It is degraded primarily by chitinivorous bacteria, which are ubiquitous in the aquatic biosphere, and include species that grow at 0°–4° C. Vibrios are the most common, widely distributed marine bacteria, and since many Vibrios are chitinivorous, the pathways and mechanisms by which they utilize chitin are of special interest.

Chitin degradation by *V. furnissii* involves several signal transducing systems, a multitude of proteins including extracellular and cytoplasmic enzymes, membrane transporters, chemoreceptors, an adhesion/deadhesion apparatus (including a lectin) that acts as a nutrient sensor, and possibly periplasmic solute binding proteins and specific porins. The genetic regulation of chitin catabolism involves a cascade, where chitin is the first and N-acetylglucosamine (GlcNAc) the final inducer. The complete pathway results in the conversion of chitin to fructose-6-P, acetate, and ammonia. However, the individual steps of the catabolic pathway remain to be elucidated. Part of the pathway is shown in FIG. 1.

2. Description of the Related Art

At least 18 species of Vibrionaceae are chitinolytic. Six are human pathogens, including *V. furnissii*, *V. cholerae* and *V. parahaemolyticus*. A brief review (1) entitled "Cholera, Copepods, and Chitinase" describes the relationships between the Vibrios, zooplankton, annual cycles of the bacteria, the invertebrates, and human disease such as food poisoning and endemic cholera. One important element in the epidemiology (2) is that *V. cholerae* adhering to chitin particles are protected from acid (equivalent to the stomach acid barrier) which kills almost all of the free-living organisms. This protection is explained by the fact that virtually all of the microbes in zooplankton "burrow" into the organism, and are not exposed to the medium (3).

Chitin and chitosan are commercial products used (especially in Japan) in medicine, agriculture, and for waste and water treatment. The polymers are used as wound dressing synthetic skin, drug delivery systems, sutures, to make contact lenses, as anticholesteremic agents, bactericidal agents, etc. (4). Chitin sutures are slowly degraded by lysozyme, and eventually absorbed, although nothing is known of the fate of the products. $(GlcNAc)_n$. $(GlcNAc)_6$ is claimed to be a potent anti-metastatic agent against mouse bearing Lewis lung carcinoma, and $(GlcNAc)_n$ activate macrophages and the immune system.

Although chitinase activities were recognized early in this century (5), the first reports on the stepwise enzymatic degradation of the polymer appear to be those of Zechmeister and Toth (6) who chromatographed extracts of almond emulsin, and of the snail, *Helix pomatia*, and separated an exo- and an endoenzyme from each. The chitinase or "polysaccharidase" converted particulate chitin to the disaccharide, N,N'-diacetylchitobiose, $(GlcNAc)_2$, and the "chitobiase," or β-N-acetylglucosaminidase (β-GlcNAcidase), hydrolyzed the disaccharide to GlcNAc. Chitin degradation continues to be intensively studied (4,5, 7). Chitinases and chitobiases are found in bacteria, fungi, plants, and animals (vertebrates and invertebrates). The structural genes encoding a number of these enzymes and some of their regulatory regions have been cloned and sequenced (5,8–21). These data show that some organisms are capable of expressing multiple chitinases, but the pathway of chitin degradation is essentially the same as that proposed in the original studies (6), i.e., virtually all investigators agree that only two enzymes are required to degrade chitin to GlcNAc (5,7). The results of the present invention with *Vibrio furnissii* differ markedly from this concept. This organism not only expresses unique hexosaminidases, but we estimate that more than two dozen proteins are required for utilization of the polysaccharide (conversion to GlcNAc-6-P).

Despite early interest in chitin utilization by marine bacteria, there are few reports on the pathway in these organisms. A chitinase gene was cloned from *Aeromonas hydrophila* (an aquatic bacterium) into *E. coli*(22); the enzyme is normally secreted by the Aeromonas into the medium, but in the transformant it traversed only the inner membrane. Zyskind et al. (23,24) cloned the β-GlcNAcidase gene from *V. harveyi* into *E. coli*, found that it was transported to the outer membrane after cleavage of a signal sequence, and that the gene sequence was similar to that of the α-chain of human β-hexosaminidase (5). In *V. harveyi*, the β-GlcNAcidase is induced by (GlcNAc)$_2$. A β-GlcNAcidase gene has also been cloned from *V. vulnificus* (25), and these researchers suggest that this single enzyme is responsible for the complete degradation of chitin to GlcNAc, although the *E. coli* transformant is unable to clear chitin on chitin/agar plates. The chitobiase gene from *V. parahaemolyticus* was cloned into *E. coli* and the enzyme purified to homogeneity (26). The purified preparation showed four closely stacked bands, which the authors speculate may result from post-translational processing at the C-terminus; the hexosaminidase was active over the pH range 4–10. Laine also reports in an Abstract from a recent meeting (27) that his laboratory has cloned a chitinase gene from *V. parahaemolyticus*; the chitinase is secreted by the *E. coli* transformant.

The following references have been cited above and their entire disclosures are hereby incorporated by reference and relied upon:

1. Nalin, D., Cholera, Copepods, and Chitinase (1976) Lancet 2: 958.
2. Nalin, D. R., Daya, V., Reid, A., Levine, M. M., and Cisneros, L., Adsorption and growth of *Vibrio cholerae* on chitin (1979), Infection and Immunity 25: 768–770.
3. Lear, D. W. in Symposium on Marine Microbiology, Carl H. Oppenheimer, edit. (1963) C. C. Thomas, publ., Springfield, Ill. P. 608.
4. Skjak-Braek, G., Anthonsen, T., and Sandford, P. (edit). Chitin and Chitosan. Sources, Chemistry, Biochemistry, Physical Properties, and Applic. (1988) Elsevier, New York. N.Y.
5. Flach, J., Pilet, P. E., Jolles, P., What's new in chitinase research? (1992) Experientia 48: 701–716.
6. Zechmeister, L., and Toth, G., Chromatographie der in der chitinreihe wirksamen Enzyme des emulsins. (1939) Enymologia 7: 165–169; Zechmeister, L., Toth, G., and Vajda, E., Chromatographie der in der chitinreihc wirksamen Enzyme der weinbergschnecke (helix pomatra). (1939) Enzyologia 7: 170–175.
7. Colowick S. P. and Kaplan N. O., Eds. Biomass, Part B, Lignin, Pectin, and Chitin. (1988) Meth. in Enzymol. 161: 403–524.
8. Joshi, S., Kozlowsld, M., Selvaraj, G., Iyer, V. N., and Davies, R. W., Cloning of the genes of the chitin utilization regulon of *Serratia liquefaciens*. (1988) J. Bacteriol. 170: 2984–2988.
9. Kuranda, K. J., and Robbins, P. W., Cloning and heterologous expression of glycosidase genes from *Saccharomyces cerevisiae*. (1987) Proc Natl. Acad. Sci. U.S.A. 84: 2585–2589.
10. Robbins, P. W., Albright, C., and Benfield, B., Cloning and expression of a *Streptomyces plicatus* chitinase (chitinase-63) in *Escherichia coli*. (1988) J. Biol. Chem. 263: 443–447.
11. Broglie, K. E., Gaynor, J. J. and Broglie, R. M., Ethylene-regulated gene expression: molecular cloning of the genes encoding an endochitinase from *Phaseolus vulgaris*. (1986) Proc Natl. Acad. Sci. U.S.A. 83: 6820–6824.
12. Fuche, R. L., McPherson, S. A., and Drahos, D. J., Clontng of a *Serratia marcescene* gene encoding chitinase. (1986) Appl. Environ. Microbiol. 51: 504–509.
13. Horwitz, M., Reid, J., and Ogrydziak D., (1984) in Chitin, chitosan, and related enzymes. akikas, J. P. Ed. Academic Press Inc., New York. pp. 191–208.
14. Korneluk R. G., Mahuran, D. J., Neote, K., Klavins, M. H., O'Dowd, B. F., Tropak, M., Willard, H. F., Anderson, M.-J., Lowden, J. A., and Gravel, R. A., Isolation of cDNA clones coding for the α-subunit of human β-hexosaminidase. Extensive homology between the α- and β-subunits and studies on Tay-Sachs disease. (1986) J. Biol. Chem. 261: 8407–8413.
15. Robbins, P. W., Trimble, R. B., Wirth, D. F., Hering, C., Maley, F., Maley, G. F., Das, R., Gibson, B. W., Royal, N., and Biemann, K., Primary structure of the Streptomyces enzyme endo-β-N-acetylglucosaminidase H. (1984) J. Biol. Chem. 259: 7577–7583.
16. Kamei, K., Yamamura, Y., Hara, S., and Ikenaka, T., Amino acid sequence of chitinase from *Streptomyces erythraeus* (1989). J. Biochem. 105: 979–985.
17. Kuranda, M. J., and Robbins, P. W., Chitinase is required for cell separation during growth of *Saccharomyces cerevisiae*. (1991) J. Biol. Chem. 266: 19758–19767.
18. Watanabe, T., Suzuki, K., Oyanagi, W., Ohnishi K., and Tanaka, H., Gene cloning of chitinase A1 from *Bacillus circulans* WL-12 revealed its evolutionary relationship to *Serratia chitinase* and to the type III homology units of fibronectin. (1990) J. Biol. Chem. 265: 15659–15665.
19. Watanabe, T., Oyanagi W., Suzuki, K., Ohnishi, K., and Tanaka, H., Structure of the gene encoding chitinase D of *Bacillus circulans* WL-12 and possible homology of the enzyme of other prokaryotic chitinases and class III plant chitinases. (1992) J. Bacteriol. 174: 408–414.
20. Delic, I., Robbins, P., and Westpheling, J., Direct repeat sequences are implicated in the regulation of two *Streptomyces chitinase* promoters that are subject to carbon catabolite control. (1992) Proc. Natl. Acad. Sci. U.S.A. 89: 1885–1889.
21. Metraux, J. P., Burkhart, W., Moyer, M., Dincher, S., Middlesteadt, W., Williams, S., Payne, G., Carnes, M., and Ryals, J., Isolation of a complementary DNA encoding a chitinase with structural homology to a bifunctional lysozyme/chitinase. (1989) Proc. Natl. Acad. Sci. U.S.A. 86: 896–900.
22. Roffey, P. E., and Pemberton, J. M., Cloning and expression of an *Aeromonas hydrophila chitinase* gene in *Escherichia coli*. (1990) Current Microbiol. 21: 329–337.
23. Soto-Gil, R. W., and Zyskind, J. W., (1984) in Chitin, chitosan and related enzymes. Zakikas J. P. Ed. Academic Press Inc., New York. pp. 209–223; Jannatipour, M., Soto-Gil, R. W., Childers, L. C., and Zyskind, J. W., Translocation of Vibrio harveyi N,N'4iacetylchitobiase to the outer membrane of *Escherichia coli*. (1987) J. Bacteriol. 169: 3785–3791.
24. Soto-Gil, R. W., and Zyskind, J. W., N,N'-diacetylchitobiase of Vibrio harveyi. Primary structure, processing, and evolutionary relationships. (1989) J. Biol. Chem. 264: 14778–14783.
25. Wortman, A. T., Somerville, C. C., and Colwell, R. R., Chitinase determinants of Vibrio vulnificus: gene cloning and applications. (1986) Appl. and Environ. Microbiol. 52: 142–145.
26. Zhu, B. C. R., Lo, J., Li, Y., Li, S., Jaynes, J. M., Gildemeister, O. S., Laine, R. A., and Ou, C., Thermostable, salt tolerant, wide pH range novel chitobiase from Vibrio parahaemolyticus: isolation, characterization, molecular cloning, and expression. (1992) J. Biochem. 112: 163–167.

27. Laine, R. A., Expression and secretion of a cloned chitinase. (1991) 5th International Conf. on Chitin and Chitosan, Abstr. 20, October 17–20, Princeton, N.J.

SUMMARY OF THE INVENTION

The present invention discloses the cloning of the genes that encode four β-N-acetylglucosaminidases involved in the catabolism of chitin in Vibrio furnissii. The functions of these enzymes in the chitin catabolic pathway are illustrated in FIG. 1. The relevant four genes are chiA which encodes extracellular chitinase (E-chitinase), endI which encodes periplasmic chitodextrinase (Endo-I), exoI which encodes periplasmic β-GlcNAcidase (Exo-I) and exoII which encodes an enzyme, aryl β-N-acetylglucosaminidase, specific for aryl β-N-acetylglucosaminides (Exo-II). In one aspect of the present invention, the complete nucleotide sequences for the chiA, the endI, the exoI, and the exoII genes from V. furnissii are disclosed.

In another aspect of the present invention, the complete amino acid sequences for the extracellular chitinase (E-chitinase), the periplasmic chitodextrinase (Endo-I), the periplasmic β-N-acetylglucosaminidase (Exo-I), and an aryl β-N-acetylglucosaminidase (Exo-II) are disclosed.

In a further aspect of the present invention, host cells transformed with the chiA gene and capable of expressing recombinant extracellular chitinase, host cells transformed with the endI gene and capable of expressing recombinant periplasmic chitodextrinase, host cells transformed with the exoI gene and capable of expressing recombinant periplasmic β-GlcNAcidase, and host cells transformed with the exoII gene and capable of expressing recombinant aryl β-N-acetylglucosaminidase are disclosed.

In another aspect of the present invention, four specific strains of V. furnissii having deletions in genes involved in the catabolic pathway of chitin are disclosed. More specifically, strains of V. furnissii having specific mutations in either the endI or the exoI genes are disclosed.

In another aspect of the present invention, a novel process for the production of specific chitin oligosaccharides is disclosed. This process involves the use of the recombinant enzymes, E. coli transformants and V. furnissii deletion mutants listed above.

DETAILED DESCRIPTION OF THE PREFERRED EMBODIMENTS

Figure 1:
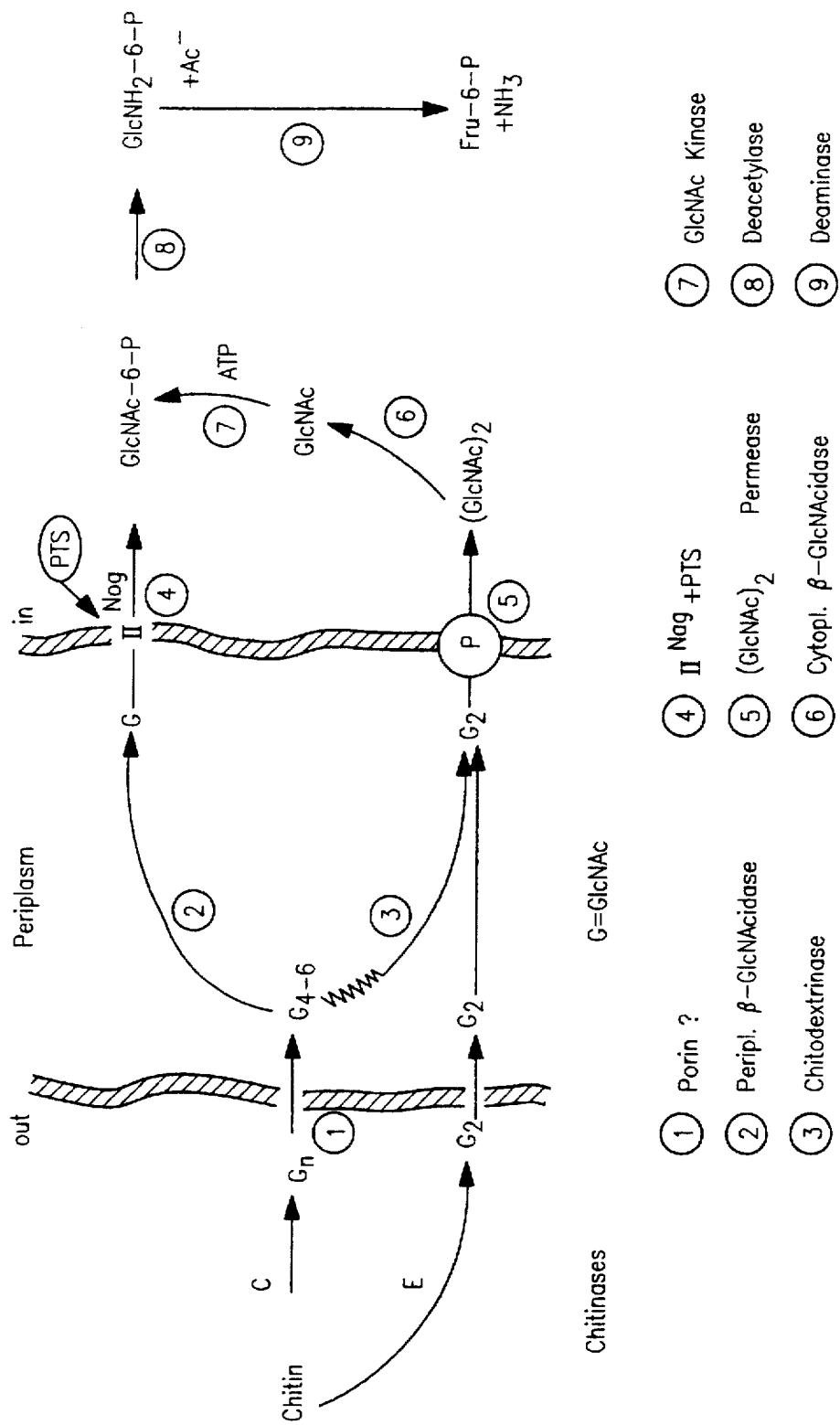
FIG. 1 is a schematic diagram of chitin degradation by V. furnissii. The enzyme Exo-II is not shown, but is presumed to split the linkage between the chitin-O-Tyr-protein and/or the chitin-O-polyphenols in invertebrate cuticles.

The cloning of each of the four genes from V. furnissii, the characterization of each isolated gene, the transformation of host cells with each isolated gene and the characterization of each recombinant β-N-acetylglucosaminidase follow. The next section (General Methods) gives details of procedures that were used for the isolation and characterization of all of the genes, while the section that follows (Specific Methods) gives specific details for each of the genes and enzymes.

GENERAL METHODS

Buffers

The composition and pH (at room temperature, unless otherwise noted) of commonly used buffers in this study are listed below.

| Buffer | Composition |
|---|---|
| EP (electroporation buffer) | 10% glycerol |
| Transformation buffer | 50 mM $CaCl_2$, 10 mM Tris-Cl, pH 7.5 |
| TE | 10 mM Tris-Cl, 1 mM EDTA, pH 8.0 |
| TAE | 40 mM Tris-acetate, 1 mM EDTA, pH 8.0, diluted from 50X stock |
| Improved TBE | 127 mM Tris, 235 mM boric acid, 2.52 mM EDTA, pH 8.3, dilute from 10X stock |
| SSC | 0.064 M NaCl, 0.012 M Na citrate, pH 7.5 |
| SHM | Used for "stringent" hybridization. 25 mM Na phosphate, pH 7.5, 5X SSC, 5% instant Carnation milk, 40% deionized formamide, 0.1 mg/ml sonicated salmon sperm DNA. |

Bacterial Culture Media

Reagents used to prepare bacterial media were purchased from Difco Labs (Detroit, Mich.). The formulations of the culture media used in this study are listed below.

| Medium | Composition (g/l) |
|---|---|
| Artificial Sea Water (ASW) | NaCl, 23.6; $Na_2SO_4$, 4; $NaHCO_3$, 0.2; KCl, 0.66; KBr, 0.96; $H_3BO_3$, 0.026; $MgCl_2.6H_2O$, 10.6; $SrCl_2.6H_2O$, 0.04; $CaCl_2$, 1.48; $K_2HPO_4$, 0.04; $NH_4Cl$, 2.0; |
| Hepes-50% ASW | Hepes buffer, 11.9 (50 mM) pH 7.5; in 50% ASW |
| Lactate-ASW | D,L-lactate, 5; in Hepes-50% ASW |
| LB | Bacto-tryptone, 10; yeast extract, 5; NaCl, 10 |
| LMB | Bacto-tryptone, 10; yeast extract, 5; NaCl, 20 |
| Marine Medium 2212 | Bacto-peptone, 5; yeast extract, 1.0; in Hepes-50% ASW |
| MacConkey | Bacto-Peptone, 17; Proteose Peptone, Agar 3; Bile Salts, 1.5; NaCl, 5; Neutral Red, 0.075; Crystal Violet, 0.5; Bacto Agar, 15 |
| M9 | $Na_2HPO_4$, 6; $KH_2PO_4$, 3; NaCl, 0.5; $NH_4Cl$, 1; $MgSO_4$, 0.24; $CaCl_2$, 0.015; carbon source, 2; Thiamine-HCl, 0.002; casamino acids, 2 |
| Medium A | $KH_2PO_4$, 4.5; $K_2HPO_4$, 10.5; $(NH_4)_2SO_4$, 1; $MgSO_4$, 0.12; carbon source, 2; Thiamine-HCl, 0.002 |

Antibiotics were used in the following concentrations ampicillin, 15 µg/ml (30 µg/ml for agar plates) and tetracycline, 5 µg/ml (10 µg/ml for agar plates).
Bacterial strains V. furnissii 7225 (available from the ATCC), a wild type strain which is also designated V. furnissii SR1519, was maintained at room temperature in a soft agar slab consisting of (g/l): yeast extract, 3; bactopeptone, 10; NaCl, 10; and agar, 5, in Hepes-buffered 50% ASW (see below). E. coli strains K-12, HB101, BL21(DE3) and XL-Blue were stored as frozen cultures in LB. Typically, strains were grown overnight in rich broth (plus appropriate antibiotics for cells containing plasmids) with vigorous shaking. Fresh medium was inoculated with cells from the overnight culture at a 1:20 or 1:50 dilution, and this culture was grown to the desired density, usually mid-exponential ($OD_{590}$=0.3–0.4).

Preparation of Bacterial Genomic DNA

Genomic DNA was prepared from *V. furnissii* SR1519 by the following procedures (28). A single colony was transferred into 100 ml of LB and grown overnight at 37° C. The cells were collected by centrifugation, resuspended in 5 ml buffer (50 mM Tris-Cl pH 8, 50 mM EDTA) and frozen at –20° C. A fresh lysozyme solution (5 mg in 0.5 ml of 0.25 M Tris-Cl pH 8) was added to the frozen cells, the mixture was thawed with gentle mixing at room temperature, and was then placed on ice for 45 min. One ml STEP solution (29) was added and the lysed cells were heated at 50° C. for 1 h; an equal volume of TE-saturated phenol was added and the layers were emulsified gently for 5 min. The aqueous and organic layers were then separated by centrifugation, and the aqueous layer was removed and re-extracted with TE-saturated phenol. The RNA and chromosomal DNA were precipitated from the aqueous phase by adding 0.1 volume of 3M NaOAc followed by 2 volumes of cold EtOH. This precipitate was spooled onto a Pasteur pipet, transferred to a clean tube and incubated overnight at 4° C. with 5 ml of buffered RNAse (50 mM Tris-Cl pH 7.5, 1 mM EDTA, 200 µg/ml RNAse A). The solution was extracted twice with an equal volume of $CHCl_3$. The DNA was reprecipitated from the aqueous phase by adding 1/10 volume of 3M NaOAc and 2 volumes of cold EtOH. The final product was suspended in TE buffer and the DNA concentration was determined as described in Plasmid Purification.

An alternate method for preparing genomic DNA was the CTAB procedure (30): In this procedure, the cells are lysed with SDS and proteinase K, and contaminants are selectively precipitated with cetyl trimethyl ammonium bromide (CTAB) in 0.5M NaCl; at this concentration of NaCl, nucleic acids are not precipitated. Residual impurities are removed by shaking with phenol, chloroform, isoamyl alcohol, and the DNA precipitated with isopropanol.

Plasmid Purification

Plasmids were prepared by the method of Pulleyblank et al. (31) or by the alkaline lysis method (30). Cells harboring the plasmid of interest were grown in LB or M9 medium containing the appropriate antibiotic. The cells were then harvested by centrifugation, and were resuspended in buffer (150 mM NaCl, 10 mM Tris-Cl pH 8) at 15 ml buffer per g wet weight of cells. The cells were lysed at room temperature by the addition of 2/3 volume of 40 mM EDTA pH 8 with 1% SDS and 1 mg/ml pronase, and the cell debris was removed by centrifugation at 150,000×g. The nucleic acids were precipitated from the supernatant fluid by the addition of 1/3 volume 40% PEG 3350 in 2M LiCl, 20 mM Tris-Cl pH 8, 2 mM EDTA. This nucleic acid pellet was homogenized in 2.5M LiCl, 10 mM Tris-Cl pH 8, 2 mM EDTA and cooled to –20° C. to precipitate RNA, which was removed by centrifugation at 250,000×g. Finally, plasmid DNA was precipitated from the supernate with 2.5 volumes of cold EtOH. The plasmid pellet was washed with 70% EtOH to remove residual salts and was dissolved in TE buffer. The nucleic acid concentration (and relative level of protein contamination) was determined by measuring the $A_{280}$ and $A_{260}$ of the preparation, where 1.0 $A_{260}$=50 µg DNA. For large scale plasmid preparations, cells were grown in 1 liter of medium, while for minipreps, cells were grown overnight in 10 ml of medium. Typically, 300–700 µg of plasmid was obtained using the large-scale protocol, and 5–10 µg from the miniprep protocol.

The alkaline lysis method is as follows: The cells are lysed in alkaline SDS, which denatures genomic and plasmid DNA. After neutralizing, the plasmid DNA is selectively renatured, and purified by treating with RNAase A, phenol/chloroform, chloroform/isoamyl alcohol, and precipitated with ethanol or PEG.

Bacterial Transformation

The heat shock procedure described in Maniatis et al. (29) was used. Host cells were grown to mid-exponential phase using an overnight culture started from a single colony. Plasmid DNA (5–50 ng in TE buffer) or DNA from a ligation mixture (10–100 ng in ligation buffer suggested by ligase manufacturer) was added (1–2 µl) to a cell suspension of 50–100 µl on ice. Occasionally, the DNA in ligation mixtures was precipitated by adding 1/10 volume of 3M sodium-acetate, pH 4.6, and 2 volumes of ice cold ethanol, followed by incubation of the samples at –70° C. for 20 min. The resultant pellet was washed once with an equal volume of 70% ethanol, dried and resuspended to 10–20 µl TE prior to use in transformation reactions. Cells with the DNA were heat shocked for 1 min at 42° C. or for 3–5 min at 37° C. in sterile glass tubes, 0.5–1.0 ml of LB was immediately added to the tubes and the cells were allowed to recover for 30–60 min at 37° C. with vigorous shaking. The transformed cells were then plated on selective media. Transformation efficiency was usually monitored by using a known amount of a control plasmid (pBR322).

An alternate transformation procedure involving electroporation was also used. The Cell-Porator® system from GIBCO-BRL and the manufacturer's recommended procedures were used (32). The Cell-Porator consists of a system for placing a suspension of cells and plasmids between two electrodes. Brief unidirectional electrical pulses render the cell membranes temporarily permeable to the DNA. Mid-exponential cells grown in LB were harvested and washed with EP and resuspended to 1/100 volume of the original culture in EP. These cells were either used immediately or frozen for later use. DNA (10–50 ng in 1–2 µl) was added to 30 µl of cells. The electroporation settings used were those recommended by the manufacturer (32). Efficiency was determined as described in the heat shock procedure.

Restriction Enzyme Digestion and Analysis of Plasmid Bacteriophage and Bacterial Genomic DNA Standard procedures were followed (29,30) for restriction enzyme digestions and analysis of the fragments generated by these digestions. Generally, 0.5–1 µg of DNA, purified as described, was digested with 1–5 U of the desired restriction enzyme under the conditions suggested by the manufacturer. In situations where digestion by more than one enzyme was desired, the digests were usually performed separately; the DNA was precipitated (by the addition of 1/10 volume 2.5 M NaOAc and 2.5 volumes of cold EtOH), dried, and the second digest was then performed. When double digestions were performed, the first enzyme used was the one requiring a lower concentration of salt; in this manner, inhibition of the second restriction enzyme (by salts remaining from the first digest) was minimized. The resulting DNA fragments, in BPB/Ficoll tracking dye, were separated by electrophoresis through 0.8% agarose gels in TAE buffer (29). Agarose gels were 13.4×14.2×0.5 cm submerged horizontal gels. The gels were run at 4–5 V per cm until the BPB dye was 2–3 cm from the bottom of the gel. DNA within the gel was visualized by soaking the gel in a 0.1 µg/ml solution of ethidium bromide for 20 min, followed by rinsing in $H_2O$ for 10 min. The gel was photographed under UV illumination with a Polaroid Land Camera (Polaroid Type 667 film). A HindIII digest of λ DNA was used for molecular weight standards.

DNA fragments were eluted from Agarose gels using standard techniques including electroelution (30), purification using GeneClean®II (Bio 101, Inc., LaJolla, Calif.) (28), and the band intercept method (29). GeneCleanII comprises a silica matrix to which DNA in cell extracts is adsorbed under conditions of high ionic strength. The matrix is washed free of protein and other contaminants, and highly purified DNA is eluted at increased temperature, low ionic strength.

Ligations were performed using standard conditions (30). Blunt-end ligations were performed at 18° C. for 18 hr, whereas compatible overhanging ends were incubated with ligase for 2 hr at 25° C. Inserts in cloning experiments were purified from gels as described above and ligated to phosphatase-treated vector that had also been cut to produce compatible ends in a ratio of 2–5:1.

pBR322 was used as the vector for much of this work, but pUC18, pUC19, and pVex were also employed. pVex is a high copy number plasmid with a T7 polymerase promoter near its multiple cloning site, thus allowing for overexpression of the desired gene product. The polymerase is generated in the host cell E. coli BL21(DE3) by induction with IPTG. Thus, in experiments involving ligations of cloned DNA fragments into pVex, induction of expression by IPTG indicates that the cloned gene is in proper orientation with respect to the T7 polymerase promoter.

DNA Sequence Analysis

The DNA prepared from the recombinant clones was sequenced by the dideoxy method using a U.S. Biochemical Sequenase sequencing kit (30,31). The kit provides buffers, labeling mixtures, termination dideoxy nucleoside triphosphates, and T7 DNA polymerase. Plasmid preparations were used in double-stranded sequencing according to the manufacturer's recommended procedures.

The V. furnissii DNA insert containing the desired gene was subcloned into two single-strand producing phagemids, the pbluescript SK+ and SK– vectors (33). These phagemids contain the intergenic (IG) region of the filamentous f1 phage, which encodes the cis-acting functions required for packaging and replication. A pBluescript recombinant transformed into E. coli with the F' episome will extrude a single-stranded f1 packaged phage when the bacterium has been infected by a helper phage. The SK+ construct extrudes the single strand corresponding to the coding strand of a β-galactosidase gene contained in the vector, while the SK– produces the other strand. This approach enables one to sequence in both directions. Single-stranded templates were prepared from pSK±constructs containing the V. furnissii gene in the vector transformed into XL1-Blue cells (34). VCSM13 was used as the helper phage to produce the single strand (33). Single-strand DNA was purified from clarified culture supernatants by PEG precipitation and by phenol/chloroform extraction (33). The radioisotopic label used in the dideoxy reactions was either α-[$^{35}$S]-dATP or α-[$^{32}$P]-dATP. Sequencing reactions were analyzed on 6–8% polyacrylamide gels run at constant power (60–70 watts) in Improved TBE buffer. Gels were fixed in 5% methanol/10% acetic acid for 20–40 min and dried for autoradiography, with exposure times of 1 to 4 days.

DNA hybridizations

DNA fragments were hybridized to one other, by the method of Southern (30), to ascertain whether they contained the same or different genes. The DNA fragments were cut from the respective plasmids with restriction enzymes and gel purified as described above. The samples were heated at 65° C. for 10 min, and 6 ng each loaded per lane of a 1% Agarose gel. Following electrophoresis, the gel was washed sequentially with 0.1M HCl (10 min), 0.5M NaOH+1.5M NaCl (2×15 min), and 0.5M Tris, pH 7.4+1.5M NaCl (2×15 min). A Southern transfer to nitrocellulose was performed overnight in 0.64M NaCl, 0.12M Na citrate, pH 7.5. The blot was allowed to dry and the original gel stained with ethidium bromide to determine whether all of the DNA had been transferred. The blots were then probed as follows. Labeled probes were prepared from the cloned genes by the random primer method (30), using a BMB Random Priming Kit® (Boehringer Mannheim Biochemicals, Indianapolis, Ind.) and α-[$^{32}$P]-dCTP. The kit contains standard DNA, hexanucleotide mixture containing all possible sequence combinations of hexanucleotides, deoxynucleoside triphosphates, and Klenow enzyme. One or more of the random hexanucleotides hybridize with the fragment to be labeled, and a strand complementary to the DNA is synthesized with labeled nucleotides (not provided in the kit) by extension of the hexanucleotide with the Klenow fragment of DNA polymerase I.

After purification (TCA precipitation, Sephadex columns), the specific activities of the probes were $10^8$–$10^9$ cpm per µg DNA. The probes (at least $10^6$ cpm aliquots each) were denatured, and hybridized to the membranes. Hybridization conditions varied from stringent to reduced stringency as follows (only the extremes are given): 65° C. overnight in 6× SSC buffer, 0.5% SDS, 5× Denhardt's solution (30), and 100 µg calf thymus DNA per ml; 37° C., 6× SSC, 10% dextran sulfate, 35% formamide. The blots were washed three times (10 min each) in 5× SSC, 0.1% SDS at 25° C., then for 60 min in 0.5 SSC, 0.1% SDS at 40° C. The blots were finally exposed to X-ray film.

Figure 2:
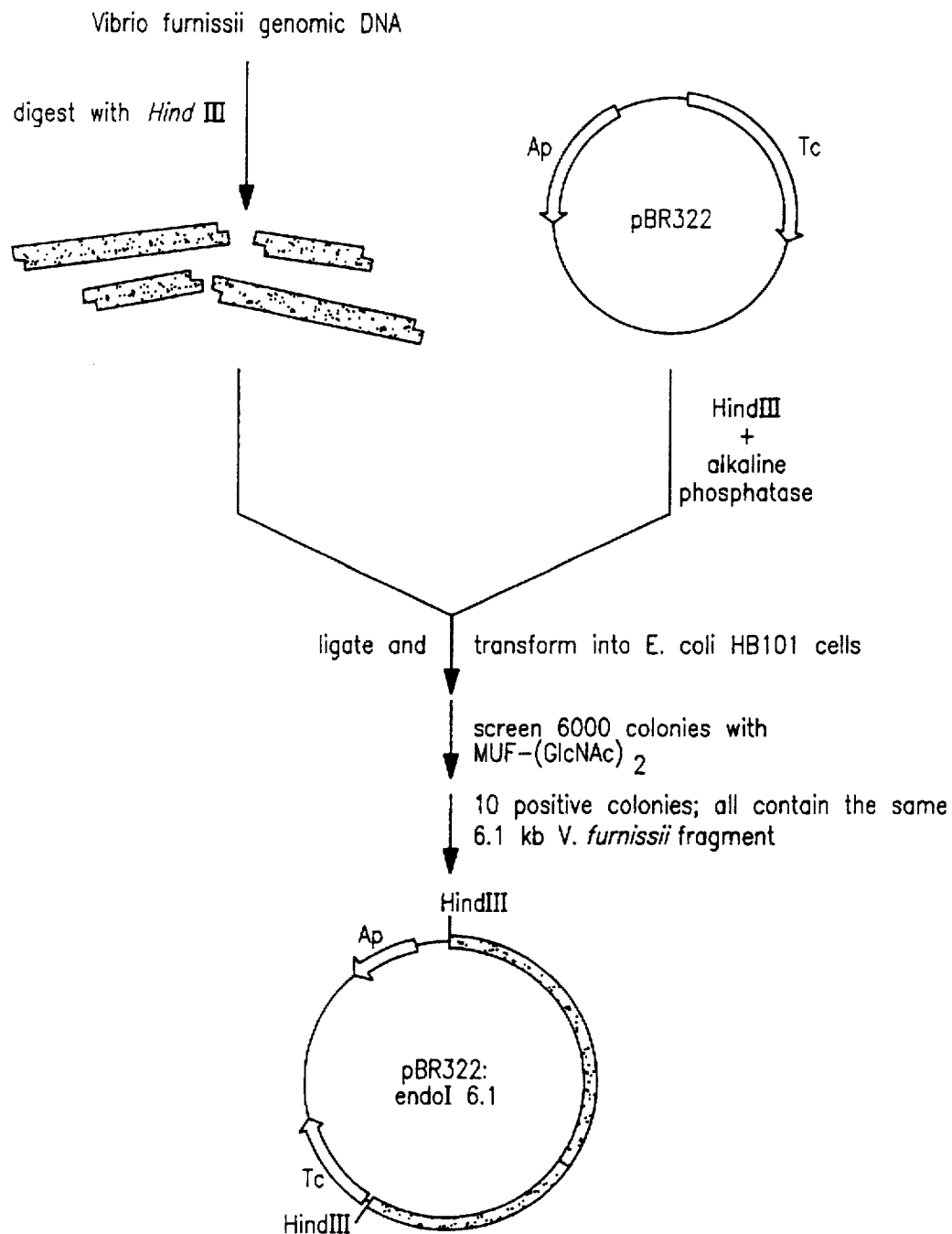
FIG. 2 summarizes the procedures used in the molecular cloning of the endI gene in V. furnissii.

SPECIFIC METHODS 1. endI gene encoding periplasmic chitodextrinase (Endo-I)
a. Cloning of endI gene encoding periplasmic chitodextrinase Aliquots (6 µg) of V. furnissii genomic DNA were digested with HindIII, extracted with phenol and CHCl$_3$/isoamyl alcohol, and EtOH precipitated. pBR322 (2 µg aliquots) was similarly digested, and dephosphorylated with bacterial alkaline phosphatase (BRL, Inc.) according to the directions of the manufacturer. As shown in FIG. 2, the digested V. furnissii and plasmid DNA were ligated with T4 DNA ligase (BRL, Inc.), and the mixture used to transform E. coli as described above (heat shock). Several ratios of the DNA preparations were tested, and the maximum number of transformants was obtained with a ratio of 3:1, V. furnissii DNA: pBR322, and the highest frequency with E. coli HB101. After 60 min of growth at 37° C. in LBA (LB ampicillin medium), aliquots were plated to determine the number of recombinant plasmids; 68% of the Amp$^r$ cells contained recombinant plasmids (Amp$^r$ Tet$^s$).

The E. coli HB101 transformants were plated on LBA, individual colonies transferred to fresh plates containing a grid, grown overnight, and a replica of each grid was transferred to a sterile Whatman No. 1 filter paper. The papers were then sprayed with 9.5 mg 4-methyl-umbelliferyl-(GlcNAc)$_2$ per ml dimethyl formamide diluted 1:50 with 0.1M Tris, pH 7.4. (4-Methyl-umbelliferyl (MUF) glycosides are not fluorescent, whereas the product of hydrolysis, MUF, is highly fluorescent (35). After spraying, the papers were incubated at 37° C. for 15 min, sprayed again with saturated NaHCO$_3$ to enhance fluorescence, and immediately viewed under low wave length U.V. light.

Transformants harboring endI were fluorescent; the colonies were picked from the original grids and single colony purified. Ten of 6,000 transformants gave positive results, and each contained an identical 6.1 Kb *V. furnissii* DNA fragment. The transformants were designated HB101:pBB22. The *V. furnissii* DNA fragment carried its own promoter as determined by cloning in both orientations in pUC vectors. The pBR322 vector carrying endI is designated pBR-EndoI.

b. Characterization of isolated endI gene

The isolated endI gene was sequenced by the SK±method described above and was found to comprise a sequence or 6180 base pairs. The entire nucleotide sequence is shown in SEQ ID NO:1. The *V. furnissii* DNA fragment contained one major open reading frame. The predicted amino acid sequence of the periplasmic chitodextrinase encoded by the endI gene is shown in SEQ ID NO:2 and consists of 1046 amino acids with a predicted molecular weight of 112.7 kDa. The predicted amino acid sequence contains a typical bacterial signal sequence for secretion into the periplasmic space (36). As described below, the protein is, in fact, processed by the *E. coli* host.

As indicated in the next section, the periplasmic chitodextrinase is an endoenzyme that cleaves soluble chitin oligosaccharides, but it is not a chitinase. Nevertheless, a search of the Swiss Protein Data Bank identified a region in the chitodextrinase, amino acid residues 300 to 700, which showed significant homology to a large number of chitinases from different sources. Eight amino acids were completely conserved in all of the homologous proteins, and in the chitodextrinase these are: Ser414, Gly416, Gly417, Phe456, Gly471, Asp473, Asp475, Asp561. Possibly, these conserved residues are at the active sites of the enzymes since they are all endo β-N-acetylglucosaminidases.

c. Characterization of recombinant periplasmic chitodextrinase

The recombinant periplasmic chitodextrinase has been purified to homogeneity from an *E. coli* transformant. The plasmid was used to transform *E. coli* BL21, grown in LBA medium, the cells extracted (French Press), nucleic acids precipitated with streptomycin, and the proteins fractionated with ammonium sulfate. The 70% fraction was chromatographed on a DEAE-sepharose column, followed by chromatography on hydroxylapatite, an ACA-34 gel filtration column, and finally on an HPLC-DEAE column. Activity was quantitated during purification by the rate of hydrolysis of p-nitrophenyl-(GlcNAc)$_2$, and the enzyme was purified 460-fold and obtained in 15% yield.

The apparent molecular weight of homogeneous Endo-I by SDS-PAGE is 120 kDa, which agrees well with the predicted mass from the nucleotide sequence, 113 kDa.

In *E. coli*, the enzyme is periplasmic. Furthermore, *E. coli* BL21 processes Endo-I by removing the first 30 amino acid residues (which are very similar to the N-terminal consensus signal sequence in *E. coli* proteins). The N-terminal amino acid sequence of the homogeneous enzyme is identical to the predicted protein sequence (from the DNA sequence), starting at residue 31 of the predicted sequence through residue 48.

The chitodextrinase is inactive with chitin, but hydrolyzes soluble (GlcNAc)$_n$. The enzyme does not liberate the GlcNAc residues that begin and terminate the oligosaccharide chain. Thus, the products of hydrolysis are (GlcNAc)$_2$ and (GlcNAc)$_3$, depending on the substrate. For example, (GlcNAc)$_4$ yields only (GlcNAc)$_2$, and (GlcNAc)$_5$ yields equimolar (GlcNAc)$_2$ and (GlcNAc)$_3$.

2. exoI gene encoding periplasmic β-GlcNAcidase a. Cloning of exoI gene encoding periplasmic β-GlcNAcidase The exoI gene was cloned into *E. coli* HB101 exactly as described above for endoI except that the screening reagent was MUF-GlcNAc instead of MUF-(GlcNAc)$_2$. Three of 6,000 *E. coli* transformants, designated HB101:pBB20, exhibited β-N-acetylglucosaminidase activity, and each contained an identical 12.5 Kb fragment of DNA that did not hybridize to the *V. furnissii* DNA fragment in the plasmid pBB22 carrying endoI.

Figure 3:
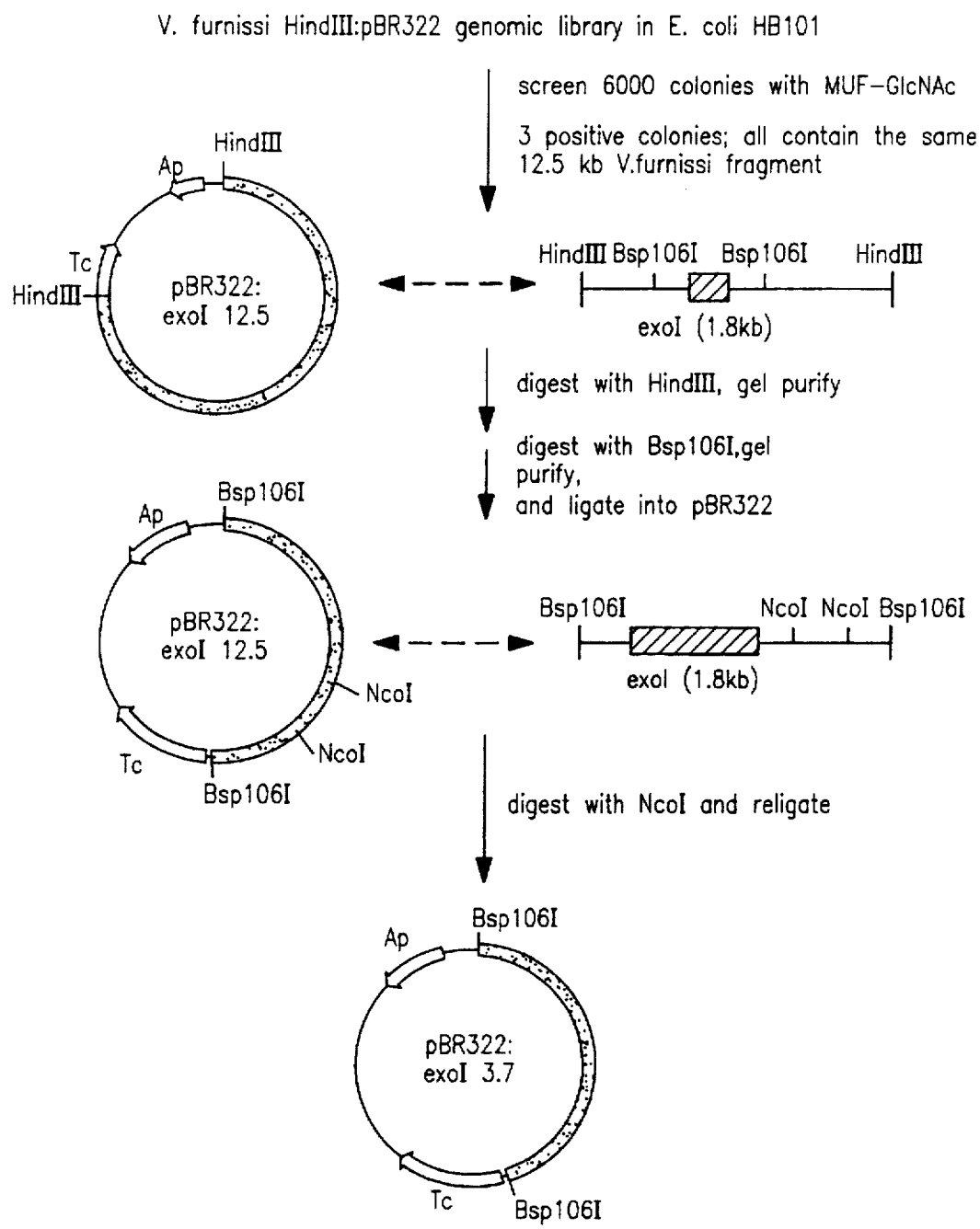
FIG. 3 summarizes the procedures used in the molecular cloning of the exoI gene in V. furnissii.

The β-GlcNAcidase gene in pBB20 was subcloned in two steps as shown in FIG. 3. The *V. furnissii* 12.5 Kb DNA fragment in pBB20 was treated with ClaI, yielding a 4.5 Kb fragment carrying exoI, which was ligated into two vectors, pBR322 and pVex, giving the constructs: pBR322:exoI4.5 and pVex:exoI4.5, respectively. The ClaI fragment was cloned into pVex in both orientations. However, only one showed a large increase in β-GlcNAcidase activity when IPTG was added to induce the T7 polymerase in *E. coli* BL21(DE3), and this clone was used for all subsequent work.

The 4.5 Kb DNA fragment contains two NcoI sites downstream from exoI. The plasmids pBR322:exoI4.5 and pVex:exoI4.5 were therefore treated with NcoI to remove 0.8 Kb of DNA, and the residual plasmids ligated to give pBR322:exoI3.7 and pVex:exoI3.7. Each plasmid carried the intact exoI gene. The 3669 bp fragment was completely sequenced.

b. Characterization of isolated exoI gene

The isolated DNA fragment containing the exoI gene in pVex:exoI3.7 was sequenced by the double stranded method, and comprises a nucleotide sequence of 3670 base pairs. The entire nucleotide sequence is shown in SEQ ID NO:3.

The open reading frame in pVex:exoI3.7 begins at nucleotide 844. There is a stop codon at 2676, putative −10 and −35 promoter regions, and a ribosome binding site. The predicted amino acid sequence of the periplasmic β-GlcNAcidase encoded by the exoI gene is shown in SEQ ID NO:4 and consists of 611 amino acids having a predicted molecular weight of 69.4 kDa.

A search of the Swiss Protein Data Bank showed 6 proteins with significant homologies to the translated open reading frame of exoI. The proteins are all hexosaminidases, including the α and β chains of human hexosaminidase. In general, the homologies were restricted to a domain in the *V. furnissii* enzyme spanning residue 200–400, and comprised about 30% identity in about a 200 amino acid overlap in the other hexosaminidases. It is important to emphasize that enzymes such as the human hexosaminidase differ considerably from the *V. furnissii* Exo-I in substrate specificity and pH optimum.

c. Characterization of recombinant periplasmic β-GlcNAcidase

In BL21(DE3):pVex:exoI3.7, the β-GlcNAcidase represents about 2.5% of the total protein in maximally induced cells (with IPTG). Exo-I was purified as described for Endo-I, omitting the hydroxylapatite step, and was obtained in homogeneous form after 40-fold purification and in 22% yield. Purification was followed by measuring the rate of p-nitrophenyl β-GlcNAc hydrolysis (PNP-GlcNAc).

The homogeneous enzyme exhibits an apparent mol. wt. of 68 kDa on SDS gels (compared to the predicted 69.4 kDA from the DNA sequence). The N-terminal 20 amino acid sequence of the homogeneous enzyme coincided exactly with the predicted sequence. Unlike Endo-I, which is a periplasmic enzyme in both *V. furnissii* and the *E. coli* transformants. Exo-I is periplasmic in the former, but not the latter. It appears that *E. coli* does not recognize the signal encoded in Exo-I.

The purified enzyme hydrolyzed aromatic glycosides of β-GlcNAc, such as PNP- and UMF-β-GlcNAc, and showed considerably lower activity on the corresponding N-acetylgalactosamine derivatives. The most active substrates were (GlcNAc)$_n$, n=3–6, and these compounds were hydrolyzed at pH optima 7–7.5. Most interestingly, at the pH of sea water, about 7.5, the enzyme showed only 2% of the activity with (GlcNAc)$_2$ compared to the other oligosaccharides. Thus, this enzyme is not a chitobiase, but it actively degrades the higher oligomers to GlcNAc and (GlcNAc)$_2$.

3. exoII gene encoding enzyme specific for aryl β-N-acetylglucosaminides a. Cloning of exoII gene encoding enzyme specific for aryl β-N-acetylglucosaminides

*V. furnissii* genomic DNA was digested with ClaI, the fragments ligated into pBR322, and the plasmids used to transform *E. coli* HB101 as described above. The transformants were screened with MUF-β-GlcNAc, exactly as described for screening the HindIII bank for the exoI gene.

Figure 4:
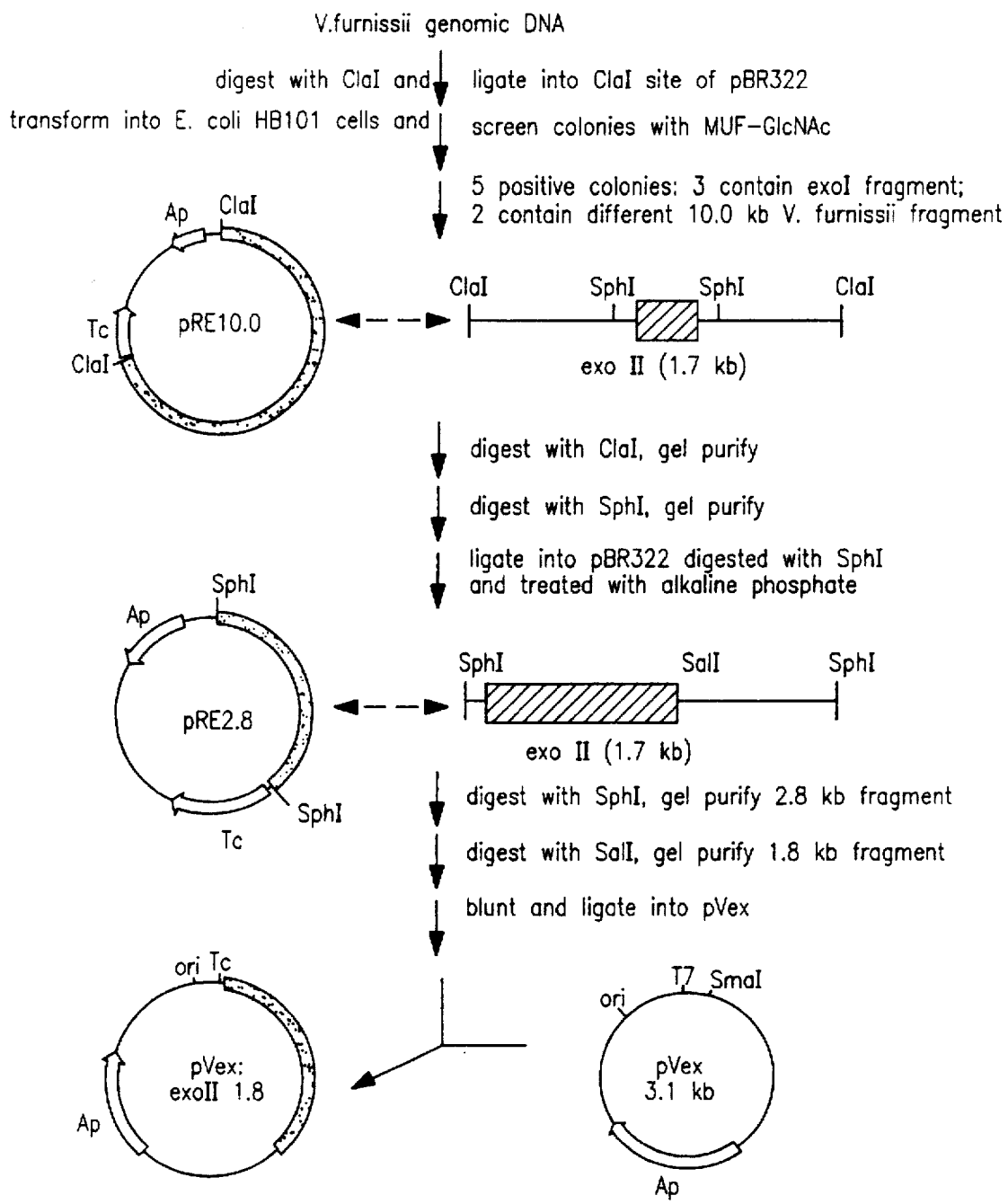
FIG. 4 summarizes the procedures used in the molecular cloning of the exoII gene in V. furnissii.

Five positive clones of 6,000 transformants were isolated and analyzed by Southern hybridization. Three clones contained exoI but two were different, and identical to one another. The two clones contained a 10.0 Kb *V. furnissii* DNA fragment (FIG. 4).

The plasmid (designated pRE100) was isolated, digested with SphI, yielding a 2.8 Kb fragment which was ligated into pBR322 and contained the exoII gene; the plasmid was designated pRE28. Finally, pRE28 was isolated, and the *V. furnissii* 2.8 Kb fragment digested with SalI, giving two fragments, 1.8 and 1 Kb respectively.

The 1.8 Kb SphI/SalI fragment was blunt ended, and ligated in both orientations into the SmaI site of pVex. Both orientations expressed Exo-II, indicating that the 1.8 Kb *V. furnissii* DNA fragment carries its own promoter; the plasmids are designated pVex:exoII1.8.

b. Characterization of isolated exoII gene

The isolated 1.7 Kb DNA fragment carrying the exoII gene was subcloned into pbluescript SK± and sequenced by the dideoxy method from single and double stranded DNA as described in "General Methods". The fragment comprised a sequence of 1713 base pairs, and the entire nucleotide sequence is shown in SEQ ID NO:5.

The 1713 base pair DNA fragment contained a single open reading frame of 984 base pairs. The start codon (residue 202) is preceded by a potential ribosomal binding site at residue 191, and −10 and −35 regions (residues 184 and 166, respectively). A potential rho independent termination signal, a region with diad symmetry (22 bp) was found following the translational termination signal.

c. Characterization of recombinant enzyme specific for aryl β-N-acetylglucosaminides The predicted amino acid sequence of the enzyme specific for aryl β-N-acetylglucosaminides encoded by the exoII gene is shown in SEQ ID NO:6 and consists of 328 amino acids having a predicted molecular weight of 36 kDa. The translational start site was confirmed by sequencing 16 N-terminal amino acids from pure recombinant protein. No apparent N-terminal secretory signal sequence is present downstream from the start site.

A computer search of protein sequences in the Swiss Prot-gene bank, showed that Exo-II is a unique β-GlcNAcidase, with no homology to other published β-GlcNAcidase sequences. However, the search revealed significant similarity to five bacterial and yeast β-glucosidases. The highest degree of similarity was found to a β-glucosidase from *Agrobacterium tumefaciens* (37). The protein shares 26% identity in a stretch of 153 amino acids. This stretch of amino acids includes the catalytic site of the β-glucosidase (25 residues). Alignment of these 25 residues (the catalytic domain) from the two proteins, reveals 44% identity.

The enzyme was purified from transformants of *E. coli* BL21. Enzymatic activity was monitored continuously by following the rate of release of nitrophenol from the substrate PNP-β-GlcNAc. The enzyme was purified to homogeneity by precipitating nucleic acids from the crude extracts with streptomycin, followed by a 0–60% ammonium sulfate precipitation of the activity, DEAE column chromatography, and finally by chromatography on Sephadex G100. The enzyme was purified 58-fold and was obtained in 83% yield.

The apparent molecular weight by SDS-PAGE was 36 kDa, which agreed with the predicted molecular weight from the gene sequence, and the N-terminal 16 amino acid sequence coincided with the predicted sequence.

The pH optimum of the enzyme is 7.0, and it catalyzes the hydrolysis of aryl (e.g., nitrophenyl) β-GlcNAc glycosides, but no other nitrophenyl glycosides tested except a slight activity on nitrophenyl β-N-acetylgalactosaminide. It was inactive with alkyl β-GlcNAc glycosides, and was completely inactive on chitin oligosaccharides. Interestingly, GlcNAc is a potent inhibitor of Exo-II.

4. chiA gene encoding extracellular chitinase a. Cloning of chiA gene encoding extracellular chitinase The chiA gene was cloned as follows. *V. furnissii* genomic DNA was digested overnight at 37° C. with NruI and the DNA fragments purified with GeneCleanII. The fragments were ligated into the vector pUC19, previously digested with SmaI followed by treatment with alkaline phosphatase and gel purified using GeneCleanII. The ligation mixture was purified with GeneCleanII, electroporated into *E. coli* JM109, and plated onto LB ampicillin plates (50 μg ampicillin/ml). The colonies were screened with a 3.0 Kb EcoRI/HindIII DNA fragment of the plasmid pJP2547 (22). The plasmid carries the chitinase gene from the marine bacterium *Aeromonas hydrophila*.

Probes were prepared from the plasmid digests thrice purified with GeneCleanII, and labeled with a BMB Random Priming Kit according to the manufacturer's instructions: the mixtures contained 25–50 ng of digested plasmid DNA, and 50 μCi [$^{32}$P]-dATP and gave probes containing 2–5×10$^8$ dpm/μg DNA. Labelled probe was separated from unincorporated nucleotides by the spun column method (30), and were denatured in 0.5M KOH at room temperature for 10 min.

Colony hybridization was carried out essentially as described by Sambrook et al. (29). Colonies were plated onto 85 mm agar plates containing the appropriate antibiotic and grown overnight at 37° C. One nitrocellulose filter (Millipore HATF 085-50) was put onto each plate and marked with India ink. The filters were removed and successively saturated with each of the following solutions: 1) 3 min with 10% SDS, 2) 5 min with 0.5M NaOH/1.5M NaCl, 3) 5 min with 0.5M Tris pH 7.4/1.5M NaCl, and 4) 5 min with 2× SSC; the filters were allowed to dry between treatments. After the final saturation with 2× SSC, the filters were dried at room temperature for 2 hours. Following U.V. crosslinking, the filters were soaked in 2× SSC for 10 min; colony debris was then soft enough to be gently scraped from the filter, using a wet tissue. The nitrocellulose discs were then prehybridized (2 hr. 37° C.), hybridized, and washed under "Stringent" conditions using the SHM mixture described above.

Hybridization was carried out for 16–20 hours at 37° C. using the denatured, labeled probe. These "Stringent" filters were then washed free of non-hybridized probe by two washes in 1× SSC/0.1% SDS, followed by two washes in 0.5× SSC/0.1% SDS at room temperature, allowing 15 minutes per wash.

Following washing, the blots were exposed to X-ray film.

Colonies which appeared to contain the desired chiA gene were picked and transferred to agar plates containing colloidal chitin. Transformants that expressed the extracellular chitinase yielded clear zones around the colonies.

Six clones which cleared the colloidal chitin after 2 days were detected from the 6000 NruI clones screened. These chitin-clearing clones also gave a strong signal for hybridization to the Aeromonas chitinase probe when compared with V. furnissii, JM109, and JM109/pUC controls.

Plasmids were isolated from the six transformants and restriction mapped; all showed an identical 3.0 Kb DNA fragment inserted into the pUC19 MCS vector. This plasmid is hereafter designated pCR-A. To ascertain that the insert contained in pCR-A was actually derived from V. furnissii, two Southern hybridizations were performed using the 3.0 Kb EcoRI/HindIII fragment from pCR-A as a probe, under "Highly Stringent" conditions (which would allow hybridization of only identical sequences). "Highly Stringent" prehybridization/hybridization mix was identical to SHM except that it contained 50% deionized formamide. The insert from PCR-A hybridized strongly to 3.0 and 7.2 Kb bands in NruI- and BglII-digested V. furnissii genomic DNA, but did not hybridize to E. coli K12 genomic DNA digested with the same enzymes. Likewise, the pCR-A-derived fragment hybridized with itself, but not with plasmids pBluescript II KS+ or SK+, pUC19, pVex, or pJP2547 (from which the Aeromonas probe had been isolated).

b. Characterization of isolated chiA gene

The entire V. furnissii insert was required for the chitin clearing phenotype; the 3.0 Kb EcoRI/HindIII fragment from PCR-A was cloned into pBluescript II KS+ and KS−, and single strand sequenced. Reactions containing dITP were included to resolve compressions which were numerous: G+C content was 63%.

The V. furnissii DNA fragment comprises a sequence of 2951 base pairs. The entire nucleotide sequence is shown in SEQ ID NO:7. The insert contains a single long open reading frame of 2598 base pairs, which would encode a gene product of 866 amino acids with a predicted molecular weight of 91.2 kDa. The predicted amino acid sequence for the extracellular chitinase encoded by the chiA gene is shown in SEQ ID NO:8.

Several regulatory regions were found in the 76 bases located 5' to the start site, including potential promoter regions (−10, −35). A predicted ribosomal binding site was found at bases 131–137. This sequence differs from the consensus (Shine and Dalgarno) by a single base substitution (AGGAAGT versus AGGAGGT). No cAMP/CPR binding site was detected in the insert, using a weighted matrix subsequence searching function of PC Gene (consensus sequence derived from data presented in de Crombrugghe et al. (38) and Ebright et al. (39)). In the sequence situated 3' to the coding region is a region with 2-fold rotational symmetry centered at base 2774 with a predicted free energy for stem-and-loop formation of $\Delta G° = -27.2$ kcal/mol. This structure resembles other prokaryotic rho-independent RNA polymerase termination signals (Rosenberg and Court, Holmes et al., (40)(41), Von Hippel et al., (42); transcription typically terminated 16–24 bases downstream from the center of the stem-loop structure (bases 2790–2798).

The chitinase gene was predicted to encode a pre-protein possessing a typical N-terminal signal sequence of 23–24 amino acids. This N-terminal sequence possesses the essential features of a standard signal peptide of the General Secretory Pathway: a short (6 amino acid) hydrophilic domain containing at least one K, a hydrophobic α-helical region rich in A and L, and a less hydrophobic C-terminal domain which terminates in ala-X-ala (36).

A search was conducted in the GenEMBL, GenBank and Swiss Prot databases for other genes and proteins having homologous nucleic acid and amino acid sequences. A high degree of homology was found between the cloned V. furnissii chitinase and chitinase A of Serratia marcescens (Koo et al., 1992, SwissProt #P07254). Of the entire S. marcescens chitinase A, 71.4% of the amino acids were identical to those in the V. furnissii chitinase; an additional 20% of the amino acids were conserved between the two; since the molecular weight of S. marcescens chitinase A is 59 kDa, homology between the two proteins extends only through the N-terminal two-thirds of the V. furnissii chitinase. A multiple alignment was performed with other homologous proteins and the V. furnissii chitinase. There is a high degree of conservation among these proteins over a 140 amino acid stretch between L256 and F396 of the V. furnissii chitinase. This region is hypothesized to contain the chitinase active site (Kuranda and Robbins (9); Watanabe et al., (18); this region of homology also encompasses two residues essential for chitinase activity (Watanabe et al., (18)). No significant homology was found between V. furnissii chitinase and plant or fungal chitinases, chitinase D of Bacillus circulans, or hexosaminidases.

Some homology was found between V. furnissii chitinase and V. furnissii periplasmic chitodextrinase (Endo-I). Although 26 gaps were introduced in order to align the sequences, the same two regions of homology noted by Kuranda and Robbins (9) are present. Additionally, one of the two "essential" amino acids, D311, is conserved between the two proteins.

c. Characterization of recombinant extracellular chitinase

The cloned protein is expressed constitutively in E. coli BL21; only about 10% of the enzyme is secreted, which is not surprising since E. coli secretes very few extracellular proteins. The enzyme was purified to homogeneity as follows.

E. coli BL21 transformants harboring the plasmid pCR-A were grown to stationary phase, and ruptured in a French Pressure Cell. The supernatant fluid was treated with streptomycin sulfate to remove nucleic acids, the proteins precipitated with solid ammonium sulfate (to 85% of saturation), and the protein pellet extracted with decreasing concentrations of ammonium sulfate. Chitinase activity was found in the 20–40% fraction, and was applied to a C4-cellufine reverse phase column. The latter was eluted with a gradient of decreasing ammonium sulfate, and active fractions were combined, dialyzed against 50 mM pyridine acetate buffer, pH 6, and adsorbed to a DEAE-Sepharose CL-6B column equilibrated with the same buffer.

The column was washed, and eluted with a linear gradient of the buffer containing increasing concentrations of NaCl, the active fractions were pooled, purified by gel filtration on a Sepharose CL-6B column, and finally chromatographed on phenyl-Sepharose CL-4B (eluted with 50 mM Tris, pH 7.5). The enzyme was purified about 33-fold, and the yield was 64%. The method of assay was to measure the rate of release of soluble counts from [$^3$H]-acetyl labeled chitin (43).

The homogeneous protein is approximately 102 kDa (SDS-PAGE), which is somewhat higher than the molecular weight predicted from the DNA sequence (91.2 kDa). Gel filtration studies show that the protein exists as a monomer. The optimum conditions for chitin hydrolysis are pH 6.0, 37°–42° C., and 50–100 mM NaCl.

N,N'-diacetylchitobiose, or $(GlcNAc)_2$, is produced from chitin, and no intermediates are detected at even the earliest time points (1 minute). After prolonged incubation of the chitin with the enzyme (1–3 days), significant quantities of GlcNAc were also detected.

5. Production of site directed deletion mutants in *V. furnissii*

The methods for the production and the characterization of each of the two specific deletion mutations in the endI or the exoI genes in *V. furnissii* are as follows.

The general procedure is to use a "suicide vector", i.e., one that cannot be replicated in *V. furnissii* because the vector lacks an origin of replication that is recognized by the host cell. In this approach, the vector contains a host gene or a fragment of the gene interrupted by an antibiotic marker. That is, the antibiotic cartridge is flanked on each side by DNA from the gene that is to be deleted. When the plasmid is transferred to *V. furnissii*, homologous recombination in each of the flanking regions results in insertion of the antibiotic cartridge into the host genome, giving a site directed null or deletion mutant.

The method of Simon et al. (44) involves conjugal transfer of plasmids from an *E. coli* mobilizing donor (IncP-type) to any Gram negative bacterium. The plasmid (e.g., a modified pACYC184) contains the Mob site for mobilization, and can only be propagated in the donor. From 5–10% of the transconjugants consisted of double crossovers, giving the desired dual recombinant null mutant.

The basic method has been improved, and used with two species of Vibrios (45–47). A vector, pNQ705 was constructed from pBR322 in which its origin of replication was deleted, and replaced with R6K Ori and therefore, pNQ705 can only be replicated in cells containing π, a protein encoded by the pir gene. An *E. coli* λ pir lysogen is used to amplify the plasmid. pNQ705 also carries the mobilizing genes required for conjugal transfer of the plasmid to another cell, $Cm^r$ and a multiple cloning site.

After amplification of the plasmid in an appropriate *E. coli* host strain, S17-1, it is transferred by conjugation into recipient cells where it cannot be replicated. Antibiotic resistant recipient cells are therefore recombinants. Miller and Mekalanos (46) used this procedure to construct site-directed mutants of *V. cholerae* toxR, and Milton et al. (47) to construct similar null mutants of a metalloprotease gene in *V. anguillarum*. In the present application, the reported procedures were modified to construct the suicide vectors, pNQT:EndoI::Cm and pNQT:ExoI::Cm. The constructs contained the following: (a) Ori R6K, an origin of replication that requires the π protein for replication; (b) the Mob RP4 genes that permit the plasmid to be transferred (mobilized) into any Gram negative recipient such as *V. furnissii*; (c) a $Tc^r$, or tetracycline resistance gene and (d) the fragment of DNA encoding endoI or exoI interrupted with the Cm or chloramphenicol resistance gene.

Two strains of *V. furnissii* were used as recipients of the conjugations, *V. furnissii* SR1519 (wild type) and *V. furnissii* AP801, a mutant in nagE (the GlcNAc permease) that has been described (48–50). A similar protocol was followed for constructing pNQT:ExoI::Cm and the corresponding null mutants. The deletion mutants were characterized by Southern blots, which showed that the $Cm^r$ cartridge had been inserted in the proper position in the *V. furnissii* genomic DNA.

a. Production and characterization of strain SR1545.15

Figure 5:
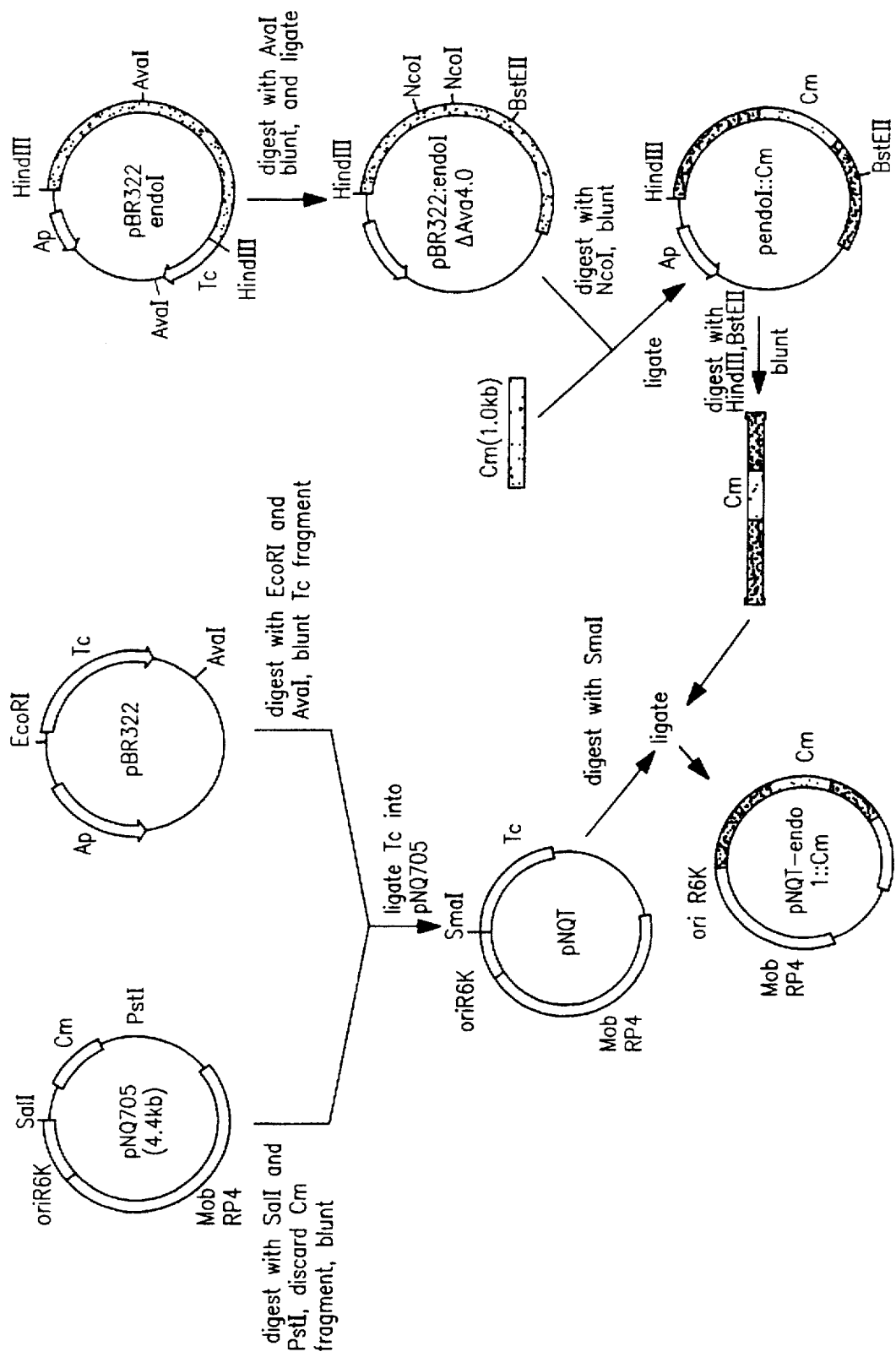
FIG. 5 outlines the procedure used to construct the plasmid pNQT:endoI::Cm.
Figure 6:
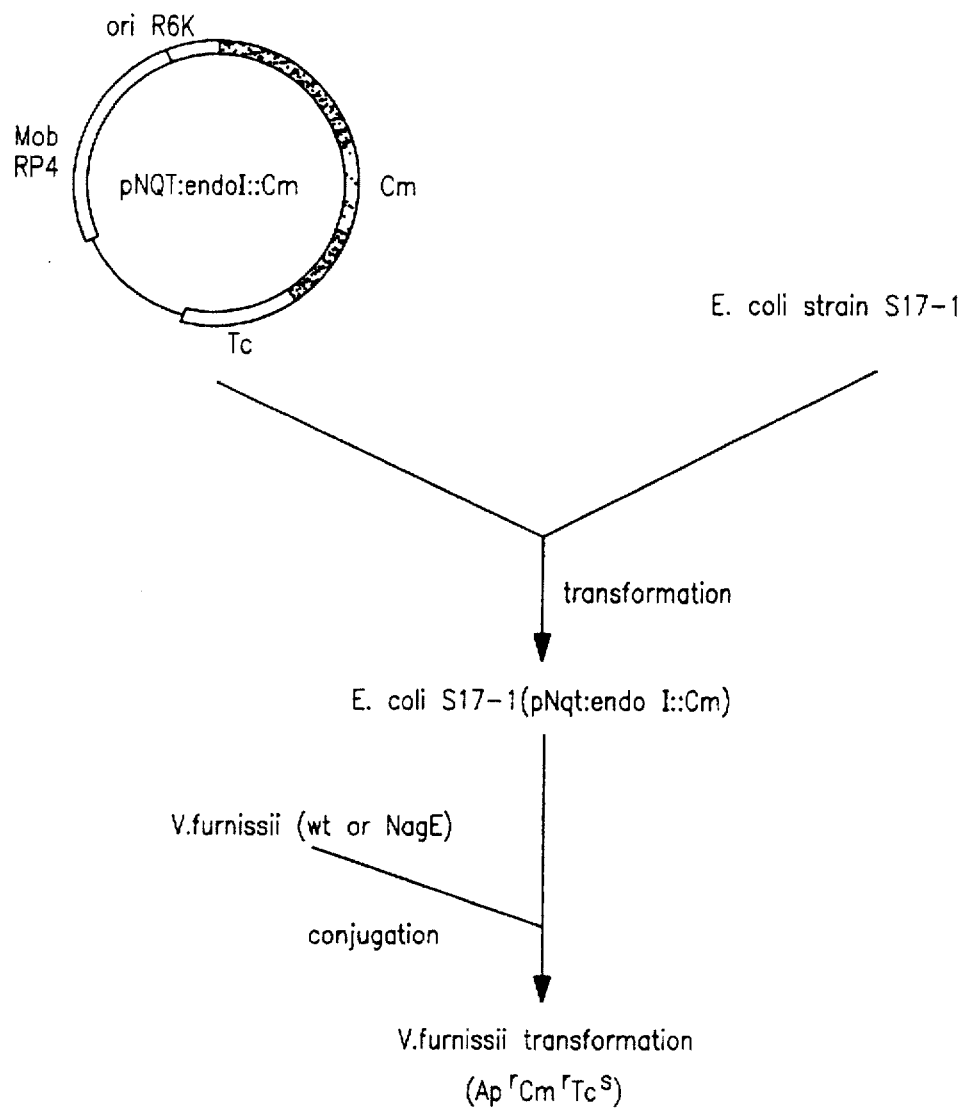
FIG. 6 outlines the procedure used to construct the V. furnissii endoI deletion mutant.

The construction of pNQT-EndoI::Cm and of the *V. furnissii* null mutants is illustrated schematically in FIGS. 5 and 6.

*V. furnissii* strain SR1545.15, or SR1519[EndoI::Cm] was prepared as follows. The wild type *V. furnissii* SR1519 was conjugated with *E. coli* S17-1, which harbored the plasmid pNQT-EndoI::Cm. The transconjugants (several thousand) were $Ap^r Cm^r Tc^s$. After purification of several clones, the genomic DNA was shown to contain the $Cm^r$ insert in endoI by the methods described above.

*V. furnissii* strain SR1545.15 has a deletion between base pairs 1670 and 2236 in the endI gene, and the $Cm^r$ gene is inserted in this region. In other words, the endI open reading frame ends at bp 1669, followed by the inserted $Cm^r$, followed by the remainder of the ORF, starting with bp 2237.

b. Production of strain SR1540.11

Strain SR1540.11 was prepared exactly as described for strain SR1545.15, except that the deletion was constructed in *V. furnissii* AP801, i.e., SR1540.11 is AP801[EndoI::Cm]. It was characterized by the same methods used for SR1545.15. Strain SR1540.11 has precisely the same deletion as SR1545.15.

c. Production and characterization of strain SR1550.304

Figure 7:
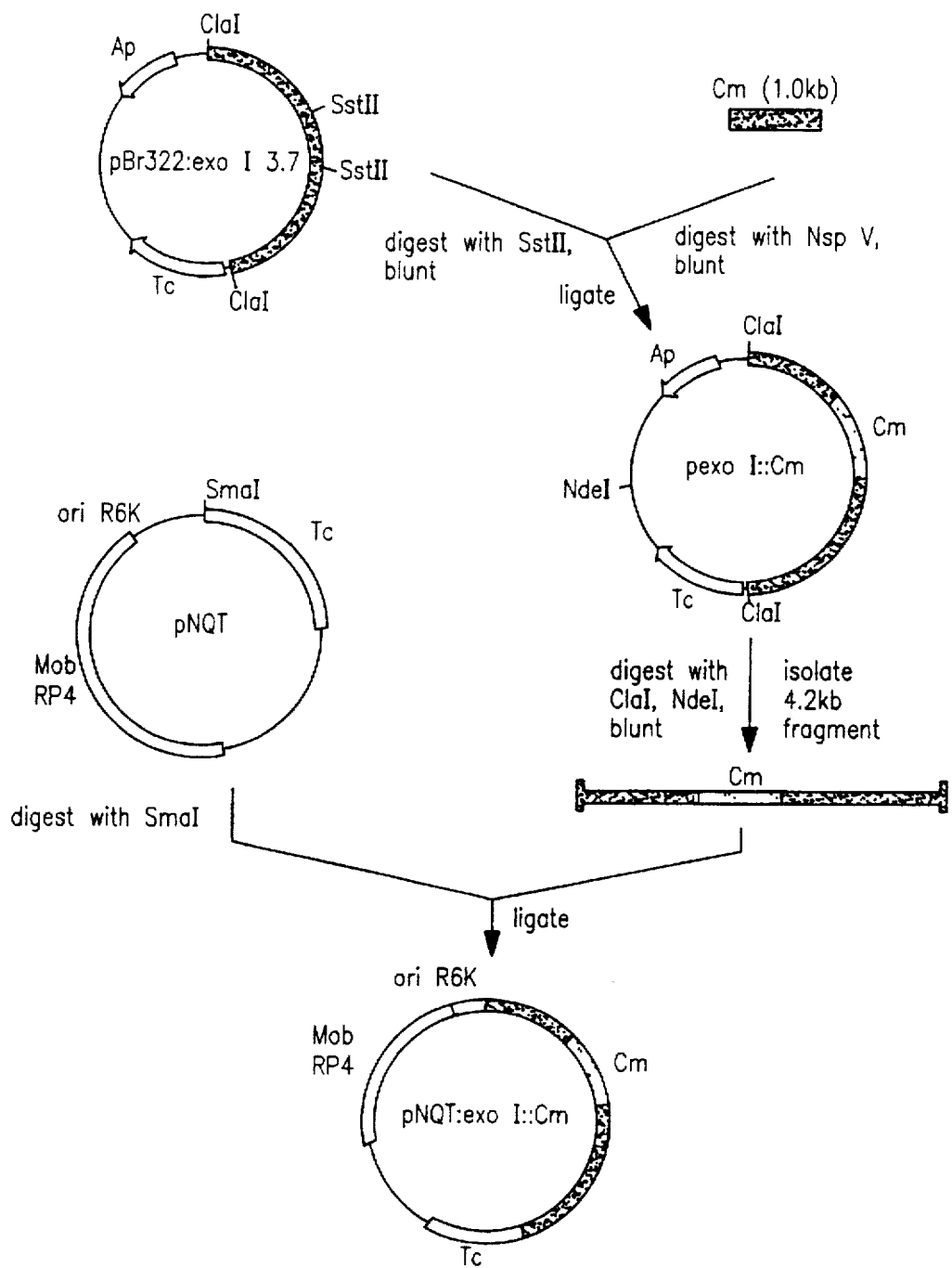
FIG. 7 outlines the procedure used to construct the plasmid pNQT:exoI::Cm.

Strain SR1550.304 was prepared as follows. The plasmid pBR322:exoI3.7 is described above, and contains the gene exoI, which expresses the enzyme ExoI. The plasmid was treated with SstII, which cuts exoI at bp 1170 and 1634. After blunt ending the two ends, they are ligated to $Cm^r$, which has also been blunt ended (FIG. 7). Thus, there are about 1.17 Kb of exoI upstream of the 5' terminus of $Cm^r$, and 2.0 Kb of exoI at the 3' terminus. The interrupted gene is then cut from the plasmid with ClaI and NdeI, blunted, and ligated into the SmaI site of pNQT, giving pNQT:ExoI::Cm. The remaining steps are exactly as described for constructing strain SR1545.15, yielding the null (deletion) mutant *V. furnissii* SR1550.304, or, SR1519[ExoI::Cm]. The deletion mutant contains $Cm^r$ inserted into exoI, which has been deleted between bp 1170–1634.

d. Production and characterization of strain SR1550.104

Strain SR1550.104 was prepared precisely as described for SR1550.304 except that the deletion was transferred by homologous recombination into the host *V. furnissii* AP801. Strain SR1550.104 is *V. furnissii* AP801 [ExoI::Cm].

6. Method for the production of specific oligosaccharides from chitin

While chitin and chitosan have been used commercially for various purposes for many years (4), the respective oligosaccharides have only recently been shown to be physiologically active. (a) Chitin oligosaccharides (derivatized at the non-reducing end with a fatty acyl group) are signals generated by the soil bacterial genus *Rhizobium*, and recognized by host leguminous plants so that nitrogen fixing nodules are formed (51). (b) Chitosan and chitin oligosaccharides induce pisatin and as many as 20 disease resistance response proteins in pea tissue and inhibit the growth of some fungal pathogens. GlcNAc and $(GlcNAc)_2$ were inactive, the trimer was slightly active, and the tetramer and pentamer were moderately active, both as antifungicides and pisatin elicitors (52,53). (c) $(GlcNAc)_6$ is a potent antimetastatic agent against mouse bearing Lewis lung carcinoma, and $(GlcNAc)_n$ activate macrophages and the immune system (13). (d) The disaccharide, $(GlcNAc)_2$, is linked to the amide group of asparagine in a large number of glycoproteins, such as those found in the blood. The disaccharide is the core to which the oligosaccharide chains of these glycoproteins are attached. Enzymes that hydrolyze the glycoprotein or glycopeptides by splitting the disaccharide (e.g., Endo A and H) or the asparagine amide (releasing the oligosaccharide) are of considerable commercial significance since they are useful for analysis and structure determination of these important macromolecules.

It is important to emphasize that the plant defense mechanisms are induced by the elicitor oligosaccharides. The multitude of proteins in the *V. furnissii* chitin catabolic cascade are likewise induced, and induction is differential. That is, higher $(GlcNAc)_n$ oligomers induce the extracellular chitinases, $(GlcNAc)_2$ induces a large number of proteins required for its catabolism but not the chitinases, and GlcNAc induces those proteins required for its metabolism but not the others. More importantly for present purposes, GlcNAc represses expression of the enzymes induced by $(GlcNAc)_2$ even when the latter is present in the medium, and $(GlcNAc)_2$ appears to repress expression of the chitinases. We emphasize, therefore, that the biological activities of chitin and chitosan oligosaccharides may be expressed by individual oligomers, but not by mixtures of oligomers, especially by mixtures containing the lower molecular weight oligosaccharides.

The reports mentioned above are, we believe, the initial reports in what is likely to become an important field in biotechnology. The oligosaccharides have use in agriculture (e.g., to induce disease resistance) and in medicine. But why has progress in this area been so slow?

The major reason is the difficulty in preparing these compounds and thus their unavailability. The costs of the commercially available oligosaccharides are prohibitive. While practical grade chitin costs from $22–49 per kilogram, the pure oligosaccharides cost from $5/mg (for $(GlcNAc)_2$) to about $15/mg (for $(GlcNAc)_6$). The problem can be illustrated with one example. We have reported (48) that $(GlcNAc)_2$ induces a large number of important proteins and enzymes in *V. furnissii*, whereas $(GlcNAc)_5$ and $(GlcNAc)_6$ induce others. The minimum concentration of $(GlcNAc)_2$ required for maximum induction is 0.6 mM in the growth medium (containing lactate or glycerol to spare the disaccharide). Thus, 0.6 mM $(GlcNAc)_2$ for one liter of medium would cost $1,270 and yield about 250 mg of induced cells (dry weight) and a few µg of each enzyme. For the experiments involving $(GlcNAc)_6$ at 0.6 mM, the cost would be $11,000 per liter!

The procedure for making these oligomers explains their cost. The first method for isolating chitosan oligomers was developed in the laboratory of the present inventors (54), as well as the method for their quantitative N-acetylation (55,56). It is surprising to find (after all these years) that the same methods are still being used commercially as indicated in the Seikagaku America, Inc., catalogue. Briefly, the procedure is as follows: purified chitin is completely deacetylated by fusion with KOH pellets under $N_2$, giving chitosan. The latter is purified by "recrystallization" 12 times to remove colored impurities, and partially hydrolyzed in 10.5N HCl at 53° C. for 72 h. The hydrolysate is applied to an ion-exchange column and eluted with a 0 to 4.2M HCl gradient. In this procedure, 5 g of chitosan were used, the ion exchange column contained 1 liter of resin, and 500 ml fractions were collected (total volume, 60 liters!). While the resolution from monomer to at least the pentamer was very good, it is obvious that the method is very limited with respect to quantity. For example, 244 mg of $(GlcNH_2)_5$ were obtained. Following quantitative N-acetylation with acetic anhydride, this quantity of material is sufficient for one 400 ml *V. furnissii* induction/growth experiment of the type described above.

Thus, this entire area of research is blocked by the unavailability of the necessary compounds. In our opinion, however, the problem can be solved by taking the following approach.

The major problem in isolating large quantities of pure oligosaccharides are the limitations in resolving mixtures of these compounds. Even E-chitinase, which hydrolyzes chitin primarily to $(GlcNAc)_2$, yields significant quantities of GlcNAc. We used wild type and genetically engineered *V. furnissii* and *E. coli* cells to remove contaminants. We have previously employed this type of method, and it works remarkably efficiently. (a) We had found (57–59) that the lower six carbon atoms of sialic acid have the configuration of N-acetylmannosamine (not previously recognized as a natural sugar), not GlcNAc as reported by several laboratories. To study the metabolism, especially the enzymatic synthesis of sialic acid, required substrate quantities of N-acetylmannosamine (ManNAc). The chemical synthesis of ManNAc (which we did) is tedious and gives small amounts of material. The problem was solved (60) by alkaline epimerization of 25 to 100 g quantities of N-acetylglucosamine; the equilibrium mixture contained 80% GlcNAc and 20% ManNAc. Part of the GlcNAc crystallized when the solution was concentrated, and the remainder (5 to 20 g, depending on the scale) was removed with *E. coli* cells induced to catabolize GlcNAc. To illustrate the power of the method, 200 mg of *E. coli* cells (dry weight) obtained from 1 liter of culture were sufficient to completely remove all of the GlcNAc from the 25 g GlcNAc epimerization mixture in 4 h at 37° C. After the incubation, the mixture was deproteinized with $Ba(OH)_2$ and $ZnSO_4$, deionized, and pure ManNAc crystallized from the concentrated supernatant fluid in 70% yield (3.5 g of the 5 g formed in the epimerization reaction). Yields up to 80% were obtained from the 100 g reaction. (b) In studies on the physical properties of the periplasmic space in *E. coli* and *Salmonella typhimurium* (61), it was necessary to remove traces of glucose and fructose from commercial (labeled and unlabeled) sucrose. The same methodology was successfully employed.

The preparation of the chitin oligosaccharides is based on similar procedures, i.e., a combination of partial hydrolysis of chitin to yield a mixture of soluble oligomers, followed by treatment with appropriate enzymes and/or mutant or transformed cells to resolve the mixtures and to obtain single products, or of desired mixtures, such as $(GlcNAc)_4$ and $(GlcNAc)_5$.

A novel method for the production of chitin oligosaccharides will be described. Before discussing these steps, it is important to emphasize that the novelty of the process is the use of intact cells, both wild type and mutants, to resolve the mixtures. Wild type *E. coli* can only utilize GlcNAc, whereas wild type *V. furnissii* can utilize $(GlcNAc)_n$, where n=1–4 without using special methods for induction. Higher oligomers such as $(GlcNAc)_5$, $(GlcNAc)_6$ and chitin are also consumed by *V. furnissii*, but only after special conditions of induction. Intact induced *V. furnissii* cells consume 0.32 µmole GlcNAc/mg protein/min at 25° C. (48), which is about the same as the maximum rate of glucose utilization by *E. coli* at 37° C. $(GlcNAc)_2$ and $(GlcNAc)_3$ are consumed at about the same rate (per GlcNAc equivalent) by *V. furnissii*. $(GlcNAc)_4$ is catabolized more slowly. $(GlcNAc)_5$ and $(GlcNAc)_6$ are not utilized unless the cells are selectively induced on swarm plates (48,50). The critical point is that *V. furnissii* catabolizes $(GlcNAc)_n$ without releasing any lower oligosaccharides, despite the fact that the first steps in their metabolism is hydrolysis in the periplasmic space. The two established pathways (mono- and disaccharide) of catabolism for the tetra- and trisaccharide are shown in FIG. 1.

The pathways for metabolizing $(GlcNAc)_5$, $(GlcNAc)_6$ and higher oligomers are not yet known. These compounds are excellent substrates for the periplasmic chitodextrinase and β-GlcNAcidase, and are very rapidly hydrolyzed in toluene permeabilized cells. Therefore, the problem in their utilization by $(GlcNAc)_2$ induced cells is that they cannot diffuse through the holes or porins in the cell envelope, the first barrier to all solutes in Gram negative bacteria. In *E. coli*, the cell envelope is penetrated by non-specific holes or porins (Omp C, Omp F, Pho E) with size limits of about 500 daltons. The molecular weights of the oligomers are: $(GlcNAc)_2$, 424; $(GlcNAc)_3$, 628; $(GlcNAc)_4$, 831; $(GlcNAc)_5$, 1,034; $(GlcNAc)_6$, 1,237. A few specific *E. coli* porins are known, such as the LamB protein, which permits diffusion of maltodextrins up to the decamer. $(GlcNAc)_2$ induces an outer membrane protein in *V. furnissii*, which may be a specific porin, and we are now cloning this gene and protein. We also believe that higher oligomers may induce other porin(s). There is no information on the non-specific porins of *V. furnissii*. Furthermore, the shapes and hydrodynamic volumes of molecules are the critical parameters in the diffusion process. However, if we make a first approximation and assume that 500 daltons is the cut-off size for solutes diffusing non-specifically through the cell envelope of *V. furnissii*, then null mutants of the inducible, specific porins would consume $(GlcNAc)_2$, but nothing larger (perhaps $(GlcNAc)_3$ at a slow rate). Similarly, if specific inducible porins that accommodate larger oligomers are deleted, only the lower oligomers would be consumed from a mixture of oligosaccharides. A critical point will be to determine the size limits of the porin presumably induced by $(GlcNAc)_5$ and $(GlcNAc)_6$. If it is similar to the Lam B protein, then mixtures of $(GlcNAc)_n$, n=1–7, would be catabolized, leaving only $(GlcNAc)_n$, n>7 in the extracellular medium.

The point to be emphasized is that porins and porin deletions or mutations in intact *V. furnissii* could serve as exquisite molecular sieves, with virtually no limit in the quantity of material that could be processed.

Two steps are required to make the oligosaccharides: (A) conversion of chitin to a mixture of soluble oligosaccharides, $(GlcNAc)_n$ and (B) resolution of the mixture to obtain single pure oligomers, or, defined mixtures, such as $(GlcNAc)_4$ and $(GlcNAc)_5$, the oligomers that are most active in inducing plant nodules (after appropriate modification).

STEP A: Chitin→soluble $(GlcNAc)_n$

Two methods give the desired products:

1. Partial acid hydrolysis of particulate chitin yields a mixture of soluble oligomers, some of which are partially deacetylated. The mixture is then quantitatively reacetylated with acetic anhydride in water (55,56).

2. A mixture of lower oligosaccharides, $(GlcNAc)_n$, n=2–4, and possibly some $(GlcNAc)_5$ are produced by the action of lysozyme on chitin (62). Egg white lysozyme is plentiful, commercially available, and quite inexpensive (about $10/gram).

STEP B: Mixed $(GlcNAc)_n$ →A single $(GlcNAc)_n$

Table I presents examples of procedures of the present invention that can be used to prepare chitin oligosaccharides. These methods result in obtaining large quantities of pure oligosaccharides by using appropriate recombinant enzymes and/or intact cells to resolve the mixtures.

TABLE I

METHODS FOR PREPARING CHITIN OLIGOSACCHARIDES

| DESIRED $(GlcNAc)_n$ | STARTING MATERIAL | STEPS | EXPECTED PRODUCTS |
|---|---|---|---|
| $(GlcNAc)_2$ | Chitin | 1. E-chitinase<br>2. *E. coli* | 1. $(GlcNAc)_2$ + (GlcNAc)<br>2. $(GlcNAc)_2$ |
| $(GlcNAc)_3$ | Soluble $(GlcNAc)_n$ | 1. Endo-I<br>2. *V. furnissii* Exo-I deletion, SR1519 | 1. $(GlcNAc)_3$ + $((GlcNAc)_2)$<br>2. $(GlcNAc)_3$ |
| $(GlcNAc)_4$ | Soluble $(GlcNAc)_n$ or chitin | 1. Exhaustive lysozyme<br>2. *V. furnissii* Endo-I deletion, SR1519 | 1. $(GlcNAc)_4$ + $((GlcNAc)_n, n = 1–3)$<br>2. $(GlcNAc)_4$ |
| $(GlcNAc)_5$ | Soluble $(GlcNAc)_n$ or chitin | 1. Partial lysozyme<br>2. *V. furnissii* Endo-I deletion, SR1519 | 1. $(GlcNAc)_5$ + $((GlcNAc)_n, n = 1–4)$<br>2. $(GlcNAc)_5$ |
| $(GlcNAc)_n$ n ≥ 5 | Soluble $(GlcNAc)_n$ | *V. furnissii* Endo-I deletion, SR1519 | $(GlcNAc)_n$ n ≥ 5 |

The normal substrate for egg white lysozyme is the N-acetylmuramyl glycosidic bond in bacterial cell walls, but it cleaves $(GlcNAc)_6$ at about 50% of this rate. The rates of cleavage of other $(GlcNAc)_n$ (relative to $(GlcNAc)_6$) are as follows: $(GlcNAc)_6$, 100; $(GlcNAc)_5$, 13; $(GlcNAc)_4$, 2.6; $(GlcNAc)_3$, 0.33; $(GlcNAc)_2$, 0.001.

The following Example describes the preparation of the disaccharide, $(GlcNAc)_2$, from chitin. Crude commercial chitin (40 g) was dissolved in concentrated HCl at 0° C., and reprecipitated by dilution in ice water. This step removes many impurities, and gives a finely divided, almost colloidal preparation of the chitin (63).

The E-chitinase preparation was the ammonium sulfate fraction from 10 g wet weight of *E. coli* BL21-chiA. The preparation in 50 mM pyridyl acetate buffer, pH 6, was dialyzed against the same buffer, mixed with the chitin preparation in the dialysis bag, and the mixture incubated for 3 days at 37° C. with stirring. Most of the precipitate was solubilized during the incubation. The dialysate was concentrated to remove the volatile buffer, yielding about 20 g of residue, consisting mostly of $(GlcNAc)_2$ and some GlcNAc. The mixture was treated as described above (for the preparation of ManNAc) with *E. coli* to remove the GlcNAc, yielding about 15 g of $(GlcNAc)_2$.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

Thus, it is to be understood that variations in the present invention can be made without departing from the novel aspects of this invention as defined in the claims.

The following references have been cited above and their entire disclosures are hereby incorporated by reference and relied upon:

28. Anonymous 1993. Protocol in GeneClean II. Abstract.
29. Sambrook, J., E. F. Fritsch, and T. Maniatis. 1982. Molecular Cloning: a Laboratory Manual. 2nd ed. Abstract.
30. Sanger, F., S. Niklen, and A. R. Coulson. 1977. DNA sequencing with chain terminating inhibitors. Proc. Natl. Acad. Sci., U.S.A. 74:5463–5467.
31. Anonymous 1993. Protocols for DNA Sequencing with Sequenase (V2.0) T7 DNA Polymerase. 7th ed. Abstract.
32. Anonymous 1991. Cell-Porator Electroporation System I. Instructions Manual and Addendum: Experimental Data: Abstract.
33. Anonymous 1992. Recovery of single stranded DNA in Stratagene protocols: pBluescript II exo-mung DNA sequencing instruction manual. Abstract.
34. Bullosck, W. O., J. M. Fernandez, and J. M. Short. 1987. XL1-Blue: A high efficiency plasmid transforming recA E. coli strain with β-galactosidase selection. BioTechniques 5:376–379.
35. O'Brien, M. and R. R. Colwell. 1987. A rapid test for chitinase activity that uses 4-methylumbelliferyl N-acetyl-B-D-glucosaminide. Appl. Environ. Microbiol. 53:1718–1720.
36. Oliver, D. B. 1987. Periplasm and Protein Secretion. In *Escherichia coli* and Salmonella typhimurium: Cellular and Molecular biology. F. G. Neidhardt, editor. American Society for Microbiology, Washington, D.C. 56–69.
37. Castle, L. A., K. D. Smith, and R. O. Morris. 1992. J. Bacteriol. 174:1478–1486.
38. deCrombrugghe, B., S. Busby, and H. Buc. 1984. Cyclic AMP receptor protein: Role in transcription activation. Science 224:831–838.
39. Ebright, R. H., P. Cossart, B. Gicquel-Sanzey, and J. Beckwith. 1984. Mutations that alter the DNA sequence specificity of the catabolite gene activator protein of E. coli. Nature 232–235.
40. Rosenberg, M. and D. Court. 1979. Regulatory sequences involved in the promotion and termination of RNA transcription. Ann. Rev. Genet. 13:319–353.
41. Holmes, M. W., T. Platt, and M. Rosenberg. 1983. Termination of transcription in *E. coli*. Cell 32:1029–1032.
42. Von Hippel, P. H., D. G. Bear, W. D. Morgan, and J. A. McSwiggen. 1984. Protein-nucleic acid interactions in transcription: a molecular analysis. Ann. Rev. Biochem. 53:389–446.
43. Cabib, E. 1988. Assay for chitinase using tritiated chitin. Methods Enzymol. 161:424–426.
44. Simon, R., U. Priefer, and A. Puhler. 1983. A broad host range mobilization system for in vivo genetic engineering: transposon mutagenesis in gram negative bacteria. Biotechnology 1:784–791.
45. Taylor, R. K., C. Manoil, and J. J. Mekalanos. 1989. Broad-host-range vectors for delivery of TnphoA: Use in genetic analysis of secreted virulence determinants of Vibrio cholerae. J. Bacteriol. 171:1870–1878.
46. Miller, V. L. and J. J. Mekalanos. 1988. A novel suicide vector and its use in construction of insertion mutations: osmoregulation of outer membrane proteins and virulence determinants in Vibrio cholerae requires taxR. J. Bacteriol. 170:2575–2583.
47. Milton, D. L., A. Norqvist, and H. Wolf-Watz. 1992. Cloning a metalloprotease gene involved in the virulence mechanism of Vibrio anguillarum. J. Bacteriol. 174:7235–7244.
48. Bassler, B. L., C. Yu, Y. C. Lee, and S. Roseman. 1991. Chitin utilization by marine bacteria: degradation and catabolism of chitin oligosaccharides by *Vibrio furnissii*. J. Biol. Chem. 266:24276–24286.
49. Yu, C., A. M. Lee, B. L. Bassler, and S. Roseman. 1991. Chitin utilization by marine bacteria: a physiological function for bacterial adhesion to immobilized carbohydrates. J. Biol. Chem. 266:24260–24267.
50. Bassler, B. L., P. J. Gibbons, C. Yu, and S. Roseman. 1991. Chitin utilization by marine bacteria: chemotaxis to chitin oligosaccharides by *Vibrio furnissii*. J. Biol. Chem. 266:24268–24275.
51. John, M., H. Rohrig, J. Schmidt, U. Wieneke, and J. Schell. 1993. Rhizobium NodB protein involved in nodulation signal synthesis is a chitinoligosaccharide deacetylase. Proc. Natl. Acad. Sci., U.S.A. 90:625–629.
52. Kendra, D. F. and L. A. Hadwiger. 1984. Characterization of the smallest chitosan oligomer that is maximally antifungal to *Fusarium solni* and elicits pisatin formation in *Pisum sativum*. Experimental Mycology 8:276–281.
53. Ryan, C. A. 1994. Commentary: Oligosaccharide signals: From plant defense to parasite offense. Proc. Natl. Acad. Sci., U.S.A. 91:1–2.
54. Horowitz, S. T., S. Roseman, and H. J. Blumenthal. 1957. The preparation of glucosamine oligosaccharides. I. Separation. J. Am. Chem. Soc. 79:5046–5049.
55. Roseman, S. and J. Ludowieg. 1954. N-Acetylation of the hexosamines. J. Am. Chem. Soc. 76:301–302.
56. Roseman, S. and I. Daffner. 1956. Colorimetric method for the determination of glucosamine and galactosamine. Anal. Chem. 28:1743–1746.
57. Comb, D. G. and S. Roseman. 1958. Composition and enenzymatic synthesis of N-acetylneuraminic acid (sialic acid). J. Am. Chem. Soc. 80:497–498.
58. Roseman, S. and D. G. Comb. 1958. The hexosamine moiety of N-acetylneuraminic acid (sialic acid). J. Am. Chem. Soc. 80:3166
59. Comb, D. G. and S. Roseman. 1960. The sialic acids. I. The structure and enzymatic synthesis of N-acetylneuraminic acid. J. Biol. Chem. 235:2529–2537.
60. Spivak, C. and S. Roseman. 1959. Preparation of N-acetyl-D-mannosamine and D-mannosamine hydrochloride. J. Am. Chem. Soc. 81:2403–2404.
61. Stock, J. B., B. Rauch, and S. Roseman. 1977. Periplasmic space in *Salmonella typhimurium* and *Escherichia coli*. J. Biol. Chem. 252:7850–7861.
62. Imoto, T., L. N. Johnson, A. C. T. North, D. C. Phillips, and J. A. Rupley. 1972. *Vertebrate Lysozymes*. 3rd Edition:666–868. Abstract.

63. Pegg, G. F. 1988. Chitinase from tomato. Methods in Enzymology (Wood and Kellogg, eds.), Vol. 181 Part B, 484–489.

SEQUENCE LISTING

SEQ ID NO:1 is the nucleotide sequence for the gene encoding periplasmic chitodextrinase.

SEQ ID NO:2 is the amino acid sequence for periplasmic chitodextrinase.

SEQ ID NO:3 is the nucleotide sequence for the gene encoding periplasmic β-GlcNAcidase.

SEQ ID NO:4 is the amino acid sequence for periplasmic β-GlcNAcidase.

SEQ ID NO:5 is the nucleotide sequence for the gene encoding aryl β-N-acetylglucosaminidase.

SEQ ID NO:6 is the amino acid sequence for aryl β-N-acetylglucosaminidase.

SEQ ID NO:7 is the nucleotide sequence for the gene encoding extracellular chitinase.

SEQ ID NO:8 is the amino acid sequence for extracellular chitinase.

What is claimed is:

1. An isolated gene which expresses aryl β-N-acetylglucosaminidase and having the nucleic acid sequence of SEQ ID NO:5.

2. A host cell which expresses recombinant aryl β-N-acetylglucosaminidase having the polypeptide sequence of SEQ ID NO:6.

3. An isolated nucleic acid encoding the polypeptide as set forth in SEQ ID NO:6.

4. An isolated nucleic acid encoding the polypeptide as set forth in SEQ ID NO:8.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 6180 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TATTCCCGTA  AAACAATAAC  TTAAGGAAAT  AAAAATGCGC  TTACATCGAG  CTAAAGTGTC      60
GAAGAGTGTC  TTTACGCTCA  GCACTTTGAC  GGCTTCGTGC  CTCATGGCGT  TCAACAGCTA     120
TGCAGCGGTG  GATTGTTCTG  CTCTGGCGGA  GTGGCAATCT  GACACAATTT  ATACTGGCGG     180
CGATCAGGTT  CAATACAACG  GGTCTGCGTA  TCAGGCCAAT  TATTGGACGC  AGAATAACGA     240
TCCGGAGCAG  TTCTCCGGTG  ATTACGCGCA  GTGGAAACTG  CTAGATGCTT  GTACGACCGA     300
CGGTGGCGAT  GACAATCAGG  CTCCCAATGC  GACATTGACC  TCTCCGTCGG  CGTCGGATGT     360
GTTGACAACC  GGAGATGTGG  TGACGCTGGC  GGCCAGCGCG  TCAGACAACG  ACGGGACGAT     420
CGCACGTGTC  GATTTTCTGG  TTGATGGTGT  GGTGGTTGCC  CAAGCGAGCA  GTGCACCCTA     480
CAGCGCCACA  TGGACGGCGG  TCGCCGGAAC  ACACCAAATC  AGCGCCATTG  CTTATGATGA     540
CAAGGCACTT  GCCAGCACGG  CGAGTCAAGT  CTCTGTTTCG  GTGACAGACA  GCACGCAACC     600
GGGCAACGAA  GCGCCAACGG  TAGACATCAC  GTTGTCTGCC  AGCCAAGTGG  ATGTGGGGGA     660
CGTGGTGACG  CTCACGGCCA  ATGCTGCAGA  CGCTGATGGC  AGTGTCGACA  AAGTTGATTT     720
TTACGTGGCC  GGCTCTCTTG  TGGGAACAGT  CGCTTCTACA  CCTTACACTT  GGATTACAC      780
CACCACCCGT  TCGGGCGCT   GGCTGTGTTT  GCGCGCGCGA  CTGATAACGT  CGGCGCGACA     840
ACGGATTCGA  CCGCGGCGAC  GCCTGACGGT  GGCTGCTGGT  CCGTGGTCAG  TACCTGTCGT     900
CCTGATGGTT  TGTATCAAAC  CGAAGGGTCA  GTGTGCCGTA  TTGTACGGTG  TACGTGAAGA     960
TGGCCGCGAG  AAAATGGGTG  CCGATCACCC  CCGTCGCGTC  ATTGGGTATT  TCACCAGTTG    1020
GCGAGCGGGA  GACGATGATC  AGACCGCTTA  CTTGGTTAAA  GACATTCCTT  GGGAACAGCT    1080
TACGCACATC  AACTACGCGT  TTGTCAGCAT  TGGTTCTGAT  GGCAAAGTCA  ATGTCGGTGA    1140
TGTCAACGAT  GCCAATAACG  CGGCGGTTGG  AAAAGAGTGG  GATGGCGTTG  AAATTGACCC    1200
AACGCTGGGC  TTTAAAGGCC  ATTTCGGCGC  ACTGGCAACC  TACAAGCAAA  AATATGGTGT    1260
GAAAACGCTG  ATCTCGATTG  GCGGCTGGGC  CGAAACGGGC  GGGCATTTTG  ACAATGATGG    1320
```

-continued

| | | | | | |
|---|---|---|---|---|---|
| CAATCGTGTT | GCGGATGGCG | GTTCTATAC | CATGACCACC | AACGCAGACG | GTTCGATTAA | 1380 |
| TCAACAAGGC | ATTGAAACCT | TGCTGATTC | CGCAGTTGAA | ATGATGCGAA | AATACCGTTT | 1440 |
| CGATGGATTG | GACATTGACC | TACGAATATC | CAACATCGAT | GGCGGGACGG | GCAATCCTGA | 1500 |
| CGACACCGCA | TTCTCTGAAT | CACGCCGTGC | TTACCTGATG | AATTCTTATC | ACGAACTGAT | 1560 |
| GCGTGTGCTG | CGTGAAAAAC | TGGATGTAGC | GAGCGCTCAA | GATGGTGTGC | ATTACATGCT | 1620 |
| GACCATTGCC | GCGCCATCAT | CGGCTTATCT | GCTACGTGGT | ATGGAAACCA | TGGCGGTGAC | 1680 |
| TCAGTACCTT | GATTACGTGA | ACATCATGTC | CTACGACTTA | CATGGTGCGT | GGAACGATCA | 1740 |
| TGTCGGTCAC | AACGCAGCAC | TGTACGACAC | CGGGAAGGAT | TCTGAACTGG | CACAATGGAA | 1800 |
| TGTGTACGGC | ACGGCGCAAT | ATGGCGGTAT | TGGTTACCTC | AACACCGATT | GGGCATTCCA | 1860 |
| CTATTTCCGC | GGTTCAATGC | CAGCGGGTCG | CATCAACATT | GGCGTGCCTT | ACTACACCCG | 1920 |
| CGGTTGGCAG | GGCGTCACTG | GTGGTGATAA | TGGCCTTTGG | GGCGCGCGGC | TTGCCAAATC | 1980 |
| AAAGCGAGTG | TCCAACCGGT | ACGGCGAGGG | CGAGAAAAAC | AACTGCGGTT | ACGGCGCGAC | 2040 |
| GGGCCTAGAT | AACATGTGGC | ACGATGTCAA | CGCCGCTGGT | GATGAGATGG | GCGCAGGTTC | 2100 |
| TAACCCAATG | TGGCATGCTA | AAAACTTGGA | GCACGGCATT | TGGGGTTCCT | ATTTAGCGGT | 2160 |
| CTATGGTTTG | GATCCAACCA | CCGCACCGTT | GGTTGGCACG | TATGCCCGTA | ATTACGACAG | 2220 |
| TGTGGCGATT | GCGCCATGGC | TTTGGAACGC | AGAGAAGAAA | GTGTTCCTGT | CGACGGAAGA | 2280 |
| CAAGCAATCC | ATTGATGTAA | AAGCAGATTA | CGTGATCGAT | AAAGAGATCG | GCGGCATCAT | 2340 |
| GTTCTGGGAA | CTCGCGGGAG | ACTACAACTG | CTACGTGCTC | GATGCCAACG | GCCAACGCAC | 2400 |
| CAGCATTGAT | AGCACGGAAC | AGGCGTGTGA | AAGCGGTCAA | GGTGAATACC | ACATGGGGAA | 2460 |
| CACCATGACC | AAAGCCATTT | ACGACAAGTT | CAAAGCGGCG | ACGCCATATG | GCAACACCGT | 2520 |
| GGCGACGGGC | GCGGTTCCGT | CTGAAACCGT | CGATATCGCT | GTGTCGATTG | GCGGTTTTAA | 2580 |
| AGTGGGCGAC | CAGAACTACC | CAATCAATCC | GAAAGTCACC | TTTACCAACA | ACACGGGCGT | 2640 |
| TGATATTCCC | GGTGGCACGG | CATTCCAGTT | CGACATTCCG | GTTTCTGCGC | CAGATAATGC | 2700 |
| CAAAGACCAA | TCGGGTGGTG | GTTTGAGCGT | GATTGCCTCT | GGTCATACGC | GTGCAGATAA | 2760 |
| CATCGGCGGT | TTGGATGGCA | CAATGCACCG | CGTCGCGTTC | TCGCTGCCTG | CGTGGAAAAC | 2820 |
| GCTACCAGCG | GGCGACACGT | ACGAGTTGGA | CATGGTGTAC | TACTTGCCGA | TTTCAGGGCC | 2880 |
| AGCAAACTAC | AGCGTGAACA | TTAACGGCGT | GGATTATGCC | TTTAAGTTTG | AACAACCTGA | 2940 |
| TTTGCCGCTC | GCGGATCTCT | CGTCAGGAAA | TGGGGGGGGC | ACCGGCGGTG | GCGACACTGG | 3000 |
| CGGCGGAACG | ACTGAGCCGG | GTGATGTTGT | GGAATGGGTA | CCCGGTTCGA | CGCAAGTGAG | 3060 |
| CGATGGCACG | ACGGTGACCT | ACAACGGCAA | GTGCTTTGTG | GCGCAAAACA | GCCCAGGCGT | 3120 |
| GTGGGAAAGC | CCAACCCAGA | CCAATTGGTT | CTGGGAGGAA | GTGACCTGCC | CGTAAAGGGA | 3180 |
| AGCCACTGTG | AAAAAACCGT | CCTTCGGGGC | GGTTTTTTGT | GTGACGGATA | AGCGATACAA | 3240 |
| CGCGCTCAGA | ACAATAGTGT | CGAATGCGAA | GCCTTAACTC | GCATGATACT | TAACTCGCTG | 3300 |
| ATAGGAGTGA | AGGCTTCGCG | TCGGCGTGAC | TCATGCATGG | CTCACGAAGG | AGGCGTGAAT | 3360 |
| TGATAGCAAA | CCGGCACCAC | CACAATCCCT | TTTTCAGAAA | TTTGGAAGCG | TTTGGCATCC | 3420 |
| TCAATTCGGT | TTAAGCCAAT | TTGCGTGTGC | GGCGGAATTT | TAACGTGCTT | GTCGATGATG | 3480 |
| CAGTTGACCA | ACTGACAACC | ATCGCCCACT | TCCACATCAT | CAAACAAAAT | GCTGTCGACA | 3540 |
| ATGGTGGCGC | CGTCGTTGAT | GCGCACACCG | GAAGAGACAA | TCGAGTGCTG | CACCGAGCCG | 3600 |
| CCCGAGTTGA | TCACGCCGTT | GGAAATGATG | GAGTTGATAA | AGATTCCTTC | ATTCCCCGTG | 3660 |
| GCCGATGACA | CCGTACGTGC | TGGCGGAAGC | TGTGGTTCGT | ACGTACGAAT | CGCCCAGTTT | 3720 |

-continued

| | | | | | |
|---|---|---|---|---|---|
| TTTTGGTACA | AATTCATGGG | CGGAACCGGC | TCAAGTAAAT | CCATATTGGC | TTCATAAAAT | 3780
| GAGTCAATCG | TGCCTACATC | GCGCCAGTAG | CAATCTTTCG | CGACGCGCCC | TTTGTCATTG | 3840
| CCAAACTGAT | ATGCGTATAC | GCTTGGGTT | GGGATCAGTT | TTGGAATGAT | GTCTTTGCCA | 3900
| AAGTCATGAC | TTGAACCACT | GTTTCTGAG | TCTTCATTCA | GCGCTTGTTG | GAGCGTTTCC | 3960
| ATATTAAAAA | TATAGATGCC | CATCGAGGCC | AAACTGCGAT | CAGGTTGTGA | AGGCATCGCG | 4020
| GGGGATCGC | TTGGCTTCTC | AACAAATGAG | GTAATACGGT | GTTCATCATC | AATGGCCATC | 4080
| ACGCCAAACG | CTTTGGCTTC | TTCGCGTGGC | ACATCCATGC | AAGCGATTGT | CAGCGTGGCG | 4140
| CCTTTCTCAA | TGTGCTCTTC | CAGCATCGCG | CATAATCCAT | GCGGTAAATA | TGATCGCCGG | 4200
| ACAGCACAAC | GACGTGCTTG | GCATCGCTGC | GTGACAGTAG | CCACATGTTG | TGAAACAGCG | 4260
| CATCGGCTGT | TCCTTCGTAC | CATTTGGCCA | CCTTTGCGCA | TTTGTGGGGG | GACCACAGTA | 4320
| ATGAACTCGC | CCAATTCGGG | GTTAAAAATG | GACCAGCCAT | CACGCAGGTG | TTTCTGCAAT | 4380
| GAATGCGATT | TGTATTGTGT | CAGCACCAAA | ATGCGGCGTA | AGCCTGAGTG | CAGACAGTTC | 4440
| GTGAGGGTAA | AATCGACTGA | TGCGATATTT | GCCGCCAAAT | GGTACGGCGG | GTTTTGCGCG | 4500
| ATCATCGGTG | AGGGGGGAAA | GTCGTGAGCC | CATACCGCCG | GCCAACACGA | CTGCTAAGGT | 4560
| ATCTTGCATC | TTTTACTCCC | TAATCATGTG | CAATTCATAA | CCACTTTAGA | GAGTAGTACA | 4620
| AGTTTCACGC | CACAATTGGA | ATGACCGTCA | AATATGGGAT | GTGCGTAGTT | TAGTTGTTAC | 4680
| TAATGCACTA | AAACAAGGCA | TCTTGTGCGT | TAAAATTGCA | CCGTGTTGGT | GCTGTGAAAA | 4740
| TAGAGGATGA | TTAAGCGAAG | TGAACCATTT | CTGCGCTGGT | GAGCACGGAG | ACGACATTTC | 4800
| GGCCTGACTC | TTTGGATTCG | TACAAGGCCA | TGGTCGGCAC | GTTGATACAC | TTCTTCAGGC | 4860
| ACTTCAGTGA | TATCCGTCAG | GCCGCCGCTG | ACGGATAAAT | CCCCTTGATG | GAGATCGAAC | 4920
| ACCGCCACGC | GAAGCCGATT | GAGGACGGTT | TCCGCTTCAT | CGATTGGTGT | GTGAGGCAAA | 4980
| ATGATGGCAA | ATTCTTCGCC | ACCAATTCGT | GCAAGAAAGT | CTGATTCGCG | CAGTTCATTG | 5040
| CGCAAACATT | GGGCAACGGC | ACGAATGGTT | TTATCGCCGC | GCGCGTGGCC | ATATTTGTCA | 5100
| TTGATGCGCT | TGAAGTGATC | AATATCGAGA | ATCGCCAAGC | ACGATTGCTC | GTGTGCCGGA | 5160
| TAGCGTTTGA | CACGCATGCA | TTCCGAGCGG | AATTCTTGAT | CAAATTTACG | TCGGTTCCAG | 5220
| ATGTTGGATA | ATCCATCTTT | TTCACTTTGG | TCACGCAATT | GGTCTTCCAG | CAACTTGCGT | 5280
| TCAGTGATGT | CAACAAACGA | CGCCACGTAG | AACTGAATGA | TGTCGTCATC | ATCCAAAATG | 5340
| GTCTGAATAC | GTAAGATCTC | CGTGAGCATC | GAGCCATCTT | TACGTTGGTT | GATCACTTCG | 5400
| CCTTCCCAGA | AGCCGTCATT | CTGCAGCGCC | TGCCACATCT | CGACATAAAA | TTCTGACGTG | 5460
| TGTTTTCCAG | AGGCAAACAT | CGATGGTTGT | TGCCCGCTCA | CTTCTTCAAA | GCTGTAGCCA | 5520
| CTCAGGCGGG | TAAACTCATT | GTTGACCTTG | ATGATGCGAT | TATTGCGGTC | GGTGATGATC | 5580
| ACCGCCGACA | TGCCATTCAT | CGCCGCGCGC | GCCAATTTAC | TCTCAATGCT | GTTTTTCTGA | 5640
| TGGTTGTTGT | TCCACAGCAC | GAAGATCGAG | GCAATCAGGC | AAATCAGCGC | AAACAGGGCA | 5700
| ACCATTTGTA | GGGTTAACGT | GTTTTGCTG | TTGTGCATCA | AGGCATGGAT | TTCGCTATTC | 5760
| TCAACACGCT | CCAATAACAC | CACCGAGGGC | ACGTTGACCA | ACGATGCGTT | TGGCGAAATC | 5820
| TTCACAAAAC | TGAACCATTG | ACCGTTTTCG | GAAATGGTGC | CTTGTTCGTC | AGAAAGAATG | 5880
| GTATGCCAAA | GCTGCGGGAA | ACGCTGCGCC | AAATTAGTGA | GCGCGGTACG | ATCGTTTGAT | 5940
| TCCTCCAGCC | GCTGACTCAT | CAACACATCC | CCGTTGAGGT | TCAGAATATC | GGGCAGCATG | 6000
| GCTCGGCGAT | TGCTGCCAGC | AATTTGCTGA | TAAATGTAGT | TCAGATTGAT | GTTTGCGACG | 6060
| AAATAGCCTT | TGCGCTCGCC | ATCAAGTTCG | ATTGGGGAGA | CAAAATAGAG | CGATGGTTTG | 6120

```
GTGGGCGTCA TGTCGTCGCC AGTCGATTGC ACACCAAACA CGCCGATTTG CCCCGCAGAC        6180
```

( 2 ) INFORMATION FOR SEQ ID NO:2:

( i ) SEQUENCE CHARACTERISTICS:
        ( A ) LENGTH: 1046 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met  Arg  Leu  His  Arg  Ala  Lys  Val  Ser  Lys  Ser  Val  Phe  Thr  Leu  Ser
 1             5                  10                  15

Thr  Leu  Thr  Ala  Ser  Cys  Leu  Met  Ala  Phe  Asn  Ser  Tyr  Ala  Ala  Val
          20                  25                  30

Asp  Cys  Ser  Ala  Leu  Ala  Glu  Trp  Gln  Ser  Asp  Thr  Ile  Tyr  Thr  Gly
     35                  40                  45

Gly  Asp  Gln  Val  Gln  Tyr  Asn  Gly  Ser  Ala  Tyr  Gln  Ala  Asn  Tyr  Trp
50                  55                  60

Thr  Gln  Asn  Asn  Asp  Pro  Glu  Gln  Phe  Ser  Gly  Asp  Tyr  Ala  Gln  Trp
65                  70                  75                              80

Lys  Leu  Leu  Asp  Ala  Cys  Thr  Thr  Asp  Gly  Gly  Asp  Asp  Asn  Gln  Ala
               85                  90                  95

Pro  Asn  Ala  Thr  Leu  Thr  Ser  Pro  Ser  Ala  Ser  Asp  Val  Leu  Thr  Thr
               100                 105                 110

Gly  Asp  Val  Val  Thr  Leu  Ala  Ala  Ser  Ala  Ser  Asp  Asn  Asp  Gly  Thr
               115                 120                 125

Ile  Ala  Arg  Val  Asp  Phe  Leu  Val  Asp  Gly  Val  Val  Ala  Gln  Ala
     130                 135                 140

Ser  Ser  Ala  Pro  Tyr  Ser  Ala  Thr  Trp  Thr  Ala  Val  Ala  Gly  Thr  His
145                 150                 155                             160

Gln  Ile  Ser  Ala  Ile  Ala  Tyr  Asp  Asp  Lys  Ala  Leu  Ala  Ser  Thr  Ala
               165                 170                 175

Ser  Gln  Val  Ser  Val  Ser  Val  Thr  Asp  Ser  Thr  Gln  Pro  Gly  Asn  Glu
               180                 185                 190

Ala  Pro  Thr  Val  Asp  Ile  Thr  Leu  Ser  Ala  Ser  Gln  Val  Asp  Val  Gly
          195                 200                 205

Asp  Val  Val  Thr  Leu  Thr  Ala  Asn  Ala  Ala  Asp  Ala  Asp  Gly  Ser  Val
     210                 215                 220

Asp  Lys  Val  Asp  Phe  Tyr  Val  Ala  Gly  Ser  Leu  Val  Gly  Thr  Val  Ala
225                 230                 235                             240

Ser  Thr  Pro  Tyr  Thr  Leu  Asp  Tyr  Thr  Thr  Thr  Arg  Ser  Gly  Arg  Trp
               245                 250                 255

Leu  Cys  Leu  Arg  Ala  Arg  Leu  Ile  Thr  Ser  Ala  Arg  Gln  Arg  Ile  Arg
          260                 265                 270

Pro  Arg  Arg  Arg  Leu  Thr  Val  Ala  Ala  Gly  Pro  Trp  Ser  Val  Pro  Val
          275                 280                 285

Val  Leu  Met  Val  Cys  Ile  Lys  Pro  Lys  Gly  Gln  Cys  Ala  Val  Leu  Tyr
     290                 295                 300

Gly  Val  Arg  Glu  Asp  Gly  Arg  Glu  Lys  Met  Gly  Ala  Asp  His  Pro  Arg
305                 310                 315                             320

Arg  Val  Ile  Gly  Tyr  Phe  Thr  Ser  Trp  Arg  Ala  Gly  Asp  Asp  Gln
               325                 330                 335

Thr  Ala  Tyr  Leu  Val  Lys  Asp  Ile  Pro  Trp  Glu  Gln  Leu  Thr  His  Ile
               340                 345                 350
```

```
Asn Tyr Ala Phe Val Ser Ile Gly Ser Asp Gly Lys Val Asn Val Gly
        355                 360                 365
Asp Val Asn Asp Ala Asn Asn Ala Ala Val Gly Lys Glu Trp Asp Gly
    370                 375                 380
Val Glu Ile Asp Pro Thr Leu Gly Phe Lys Gly His Phe Gly Ala Leu
385                 390                 395                 400
Ala Thr Tyr Lys Gln Lys Tyr Gly Val Lys Thr Leu Ile Ser Ile Gly
                405                 410                 415
Gly Trp Ala Glu Thr Gly Gly His Phe Asp Asn Asp Gly Asn Arg Val
            420                 425                 430
Ala Asp Gly Gly Phe Tyr Thr Met Thr Thr Asn Ala Asp Gly Ser Ile
            435                 440                 445
Asn Gln Gln Gly Ile Glu Thr Phe Ala Asp Ser Ala Val Glu Met Met
    450                 455                 460
Arg Lys Tyr Arg Phe Asp Gly Leu Asp Ile Asp Leu Arg Ile Ser Asn
465                 470                 475                 480
Ile Asp Gly Gly Thr Gly Asn Pro Asp Asp Thr Ala Phe Ser Glu Ser
                485                 490                 495
Arg Arg Ala Tyr Leu Met Asn Ser Tyr His Glu Leu Met Arg Val Leu
            500                 505                 510
Arg Glu Lys Leu Asp Val Ala Ser Ala Gln Asp Gly Val His Tyr Met
        515                 520                 525
Leu Thr Ile Ala Ala Pro Ser Ser Ala Tyr Leu Leu Arg Gly Met Glu
    530                 535                 540
Thr Met Ala Val Thr Gln Tyr Leu Asp Tyr Val Asn Ile Met Ser Tyr
545                 550                 555                 560
Asp Leu His Gly Ala Trp Asn Asp His Val Gly His Asn Ala Ala Leu
            565                 570                 575
Tyr Asp Thr Gly Lys Asp Ser Glu Leu Ala Gln Trp Asn Val Tyr Gly
            580                 585                 590
Thr Ala Gln Tyr Gly Gly Ile Gly Tyr Leu Asn Thr Asp Trp Ala Phe
        595                 600                 605
His Tyr Phe Arg Gly Ser Met Pro Ala Gly Arg Ile Asn Ile Gly Val
    610                 615                 620
Pro Tyr Tyr Thr Arg Gly Trp Gln Gly Val Thr Gly Gly Asp Asn Gly
625                 630                 635                 640
Leu Trp Gly Ala Arg Leu Ala Lys Ser Lys Arg Val Ser Asn Arg Tyr
                645                 650                 655
Gly Glu Gly Glu Lys Asn Asn Cys Gly Tyr Gly Ala Thr Gly Leu Asp
            660                 665                 670
Asn Met Trp His Asp Val Asn Ala Ala Gly Asp Glu Met Gly Ala Gly
        675                 680                 685
Ser Asn Pro Met Trp His Ala Lys Asn Leu Glu His Gly Ile Trp Gly
    690                 695                 700
Ser Tyr Leu Ala Val Tyr Gly Leu Asp Pro Thr Thr Ala Pro Leu Val
705                 710                 715                 720
Gly Thr Tyr Ala Arg Asn Tyr Asp Ser Val Ala Ile Ala Pro Trp Leu
                725                 730                 735
Trp Asn Ala Glu Lys Lys Val Phe Leu Ser Thr Glu Asp Lys Gln Ser
            740                 745                 750
Ile Asp Val Lys Ala Asp Tyr Val Ile Asp Lys Glu Ile Gly Gly Ile
            755                 760                 765
Met Phe Trp Glu Leu Ala Gly Asp Tyr Asn Cys Tyr Val Leu Asp Ala
```

|                    |                    |                    |
|--------------------|--------------------|--------------------|
| 770                | 775                | 780                |

Asn Gly Gln Arg Thr Ser Ile Asp Ser Thr Glu Gln Ala Cys Glu Ser
785                 790                 795                 800

Gly Gln Gly Glu Tyr His Met Gly Asn Thr Met Thr Lys Ala Ile Tyr
                  805                 810                 815

Asp Lys Phe Lys Ala Ala Thr Pro Tyr Gly Asn Thr Val Ala Thr Gly
              820                 825                 830

Ala Val Pro Ser Glu Thr Val Asp Ile Ala Val Ser Ile Gly Gly Phe
          835                 840                 845

Lys Val Gly Asp Gln Asn Tyr Pro Ile Asn Pro Lys Val Thr Phe Thr
    850                 855                 860

Asn Asn Thr Gly Val Asp Ile Pro Gly Gly Thr Ala Phe Gln Phe Asp
865                 870                 875                 880

Ile Pro Val Ser Ala Pro Asp Asn Ala Lys Asp Gln Ser Gly Gly Gly
              885                 890                 895

Leu Ser Val Ile Ala Ser Gly His Thr Arg Ala Asp Asn Ile Gly Gly
              900                 905                 910

Leu Asp Gly Thr Met His Arg Val Ala Phe Ser Leu Pro Ala Trp Lys
        915                 920                 925

Thr Leu Pro Ala Gly Asp Thr Tyr Glu Leu Asp Met Val Tyr Tyr Leu
930                 935                 940

Pro Ile Ser Gly Pro Ala Asn Tyr Ser Val Asn Ile Asn Gly Val Asp
945                 950                 955                 960

Tyr Ala Phe Lys Phe Glu Gln Pro Asp Leu Pro Leu Ala Asp Leu Ser
              965                 970                 975

Ser Gly Asn Gly Gly Gly Thr Gly Gly Gly Asp Thr Gly Gly Gly Thr
          980                 985                 990

Thr Glu Pro Gly Asp Val Val Glu Trp Val Pro Gly Ser Thr Gln Val
        995                 1000                1005

Ser Asp Gly Thr Thr Val Thr Tyr Asn Gly Lys Cys Phe Val Ala Gln
    1010                1015                1020

Asn Ser Pro Gly Val Trp Glu Ser Pro Thr Gln Thr Asn Trp Phe Trp
1025                1030                1035                1040

Glu Glu Val Thr Cys Pro
              1045

( 2 ) INFORMATION FOR SEQ ID NO:3:

( i ) SEQUENCE CHARACTERISTICS:
      ( A ) LENGTH: 3670 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
| GGTGGTGGCA | CCTCCTGCCG | CGCGGTATTC | GGCATGCGTC | CGGCGTTTGA | TTGGCGACAG | 60 |
| GACCGGCAGC | GCCAACCTGT | TGCTTGGCGT | GGAACGCGAT | GGACGCCGTC | ATTCACGCCA | 120 |
| TCACCTTAGC | TGCCGAACAA | GGCGGCCTGA | ATAACGATAA | CTTTGGTCAA | CTGCACGTGG | 180 |
| GCTTGGCGCT | GGCTGGCGTG | AGCACCAAGC | GACTTGGCAT | GCTTTATGCA | ATTGCCACAC | 240 |
| CGTTTGCGTC | GCTCACGCTC | AATACCGATG | CCTATGGTGC | GTGCCTCGGT | GCGCACCACG | 300 |
| GTGACAACGG | CGCCATCATG | ATTGCTGGCA | CGGGCTCATG | CGGTTTGTTC | TTGCAAGACG | 360 |
| GCCACCAGCA | CGTGGTGGGG | GGACGTGAGT | TCCCGATCTC | CGATGAGGGC | AGTGGCGCGG | 420 |

```
TGATGGGACT GCGCCTGATT CAACAAGTGC TGCTGATTGA AGATGGTATT TATCCGGCCA    480
CGCCACTTAG TCAGTGTGTC ATGCAGCATT GACACGATGT GACGCCATTG TCGCTTGGTC    540
GAAATCCGCT TTACCTCGCG ACTATGGTCA ATTTCGCCG CAGATTTTCG CGTTGGCGAA     600
TCAAGGTGAC ACGCTAGCAA TATCCCTGCT GAAACAGACA GCAGCGGATA TCGAAATGTT    660
TTTGAACGCC CTGCATCGCA AAGGGGCACA GCGAATCTGC TTCATGGGCA GCATCGCGGA    720
ACGCATTCAC GCATGGTTAT CCCCTCCCGT TCAGCAATGG ATCGTCGCAC CGCAAGCGGA    780
TGCGATGGAG GGCGCATTAA TGTTTGCCGG CAAAGCCGAG CATAATTTGT ATTAAGGGTT    840
GCTCATGAAC TATCGAATAG ACTTCGCGGT ATTGTCAGAA CATCCACAGT TCTGCCGTTT    900
TGGCTTGACG CTGCATAACC TCAGCGATCA GGACTTAAAG GCCTGGAGCC TGCATTTCAC    960
CATCGATCGC TACATTCAGC CCGATAGCAT CAGTCACAGC CAGATTCATC AAGTCGGCAG   1020
TTTCTGTTCG CTCACGCCGG AGCAGGACGT GATAAATTCC AACAGCCATT TCTACTGCGA   1080
ATTCAGCATC AAAACCGCGC CGTTTCCGTT TCACTATTAC ACCGACGGCA TCAAAGCCGC   1140
GTTTGTCCAA ATTAATGATG TAGAGCCGCG GGTTCGTCAC GACGTGATCG TCACCCCCAT   1200
CGCACTCGCC TCCCCCTATC GGGAACGCAG CGAGATCCCG GCCACGGATG CCGCGACGTT   1260
GAGCCTGTTA CCCAAACCCA ATCATATCGA ACGCTTGGAT GGTGAATTTG CCCTTACCGC   1320
CGGCAGCCAG ATTTCATTGC AATCCTCTTG TGCAGAAACT GCCGCCACGT GGCTCAAGCA   1380
AGAACTGACG CATCTCTATC AGTGGCAGCC ACGATATT GGCAGCGCCG ACATTGTGCT    1440
ACGCACCAAC CCAACGCTGG ATGAAGGCGC CTATCTGCTG TCAGTCGACC GCAAACCTAT   1500
TCGTTTGGAA GCCAGCAGTC ACATCGGCTT TGTCCATGCC AGTGCGACAT TGCTGCAATT   1560
GGTTCGCCCA GATGGCGACA ACCTGCTGGT GCCACACATC GTTATCAAAG ACGCACCGCG   1620
CTTTAAATAC CGCGGCATGA TGCTGGATTG CGCGCGTCAT TTTCATCCGC TGGAGCGCGT   1680
TAAACGCCTC ATCAACCAAC TGGCGCATTA CAAATTCAAC ACCTTTCATT GGCATCTGAC   1740
CGATGATGAA GGTTGGCGCA TTGAAATTAA GTCTCTACCT CAATTGACCG ACATTGGCGC   1800
GTGGCGCGGT GTGGATGAAG TCCTGGAACC GCAATACAGC CTGCTGACCG AAAAACACGG   1860
TGGCTTTTAC ACCCAAGAGG AGATCCGTGA AGTGATCGCC TACGCCGCAG AACGCGGCAT   1920
CACGGTGATT CCAGAAATTG ACATTCCCGG TCACAGCCGA GCGGCGATCA AGCCTTACC    1980
GGAATGGCTA TTTGACGAAG ATGACCAATC ACAATACCGC AGCATTCAGT ACTACAACGA   2040
CAACGTGCTA TCGCCAGCCC TGCCCGGCAC CTACCGTTTT CTCGATTGCG TATTGGAGGA   2100
AGTGGCCGCG CTGTTTCCGA GCCATTTCAT TCACATTGGC GCCGATGAAG TGCCAGATGG   2160
CGTGTGGGTC AACAGCCCGA AATGTCAGGC ATTGATGGCA GAAGAGGGCT ACACCGACGC   2220
CAAAGAGTTA CAAGGGCACC TGCTGCGCTA TGCGGAGAAG AAGCTCAAAT CACTCGGCAA   2280
ACGCATGGTC GGTTGGGAAG AAGCGCAGCA TGGTGACAAA GTCAGCAAAG ATACCGTGAT   2340
TTATTCTTGG TTATCCGAAC AAGCCGCACT GAACTGCGCC CGTCAAGGGT TTGATGTCAT   2400
TTTACAACCG GGACAGTTTA CGTACCTCGA CATTGCGCAA GACTACGCGC CAGAAGAGCC   2460
GGGCGTCGAC TGGGCTGGCG TGACGCCACT GGAGCGCGCC TATCGCTACG AGCCGCTGGT   2520
CGAGGTGCCA GAACACGACC CGCTGCGCAA ACGCATTTTG GGGATTCAGT GCGCGCTGTG   2580
GTGTGAACTG GTCAACAATC AAGACCGCAT GGACTACATG ATCTATCCGC GTTTGACCGC   2640
ACTGGCGGGA AGCGGCTTGG ACACAAAAAT CCCAGCGTGA TTGGCTGGAT TACCTGGCGC   2700
GCCTCAAAGG CCATTTACCC CAACTTGATC AACAAGGCAT CCGCTACCGG GCGCCTTGGA   2760
AAGCATAACG CAACACGTTT TCTCTAGCAT CGACATTGAG TGGCGCCAAT GCGCCACTGT   2820
```

```
TTAAAAAGGA  AATTACCATG  AAATACGGCT  ATTTCGATAA  CGACAATCGC  GAATACGTCA    2880

TTACTCGTCC  CGATGTTCCT  GCACCTTGGA  CCAACTACCT  CGGCACGGAA  AAATTCTGCA    2940

CCGTCATCTC  CCATAATGCG  GGGGGCTACT  CGTTCTATCA  CTCACCCGAG  TACAACCGTG    3000

TGACCAAGTT  CCGTCCGAAC  TTCACACAAG  ATCGTCCCGG  GCATTACATC  TATTTGCGCG    3060

ATGATGAAAC  CGGTGATTTC  TGGTCGGTCT  CTTGGCAGCC  CGTTGCCAAA  AACCTTGACG    3120

ATGCCCATTA  CGAAGTGCGC  CATGGATGCC  GTGTATGAGT  ATCTGTTCTC  CCCATACGGT    3180

TTACACCTCA  ACGCCCCCTC  GTTTGCAACG  CCCAACGATG  ACATCGGTTT  TGTCACCCGC    3240

GTCTACCAAG  GCGTGAAAGA  AAACGGTGCG  ATTTTCTCGC  ATCCGAACCC  GTGGGCATGG    3300

GTCGCCGAAG  CCAAACTGGG  ACGCGGTGAT  CGCGCGATGG  AATTCTACGA  TTCGCTCAAC    3360

CCATACAACC  AGAACGACAT  CATTGAAACG  CGCGTGGCAG  AGCCATATTC  CTACGTGCAA    3420

TTCATCATGG  GTCGCGACCA  CCAAGATCAC  GGCCGTGCAA  ACCACCCTTG  GCTCACCGGT    3480

ACATCGGGCT  GGGCCTACTA  CGCGACCACC  AACTTCATTT  TGGGAGTGCG  TACCGGATTT    3540

GACAGGTTGA  CCGTGGATCC  ATGTATTCCT  GCCGCTTGGT  CGGGCTTTGA  GCGTCACGCG    3600

CGAGTGGCGC  GGTGCGACGT  ATCACATGTC  AGTCCAAAAC  CCGAATGGCG  TCAGCAAAGG    3660

CGTGCAATCG                                                                3670
```

(2) INFORMATION FOR SEQ ID NO:4:

(i) SEQUENCE CHARACTERISTICS:
        (A) LENGTH: 611 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Asn Tyr Arg Ile Asp Phe Ala Val Leu Ser Glu His Pro Gln Phe
 1               5                  10                  15

Cys Arg Phe Gly Leu Thr Leu His Asn Leu Ser Asp Gln Asp Leu Lys
            20                  25                  30

Ala Trp Ser Leu His Phe Thr Ile Asp Arg Tyr Ile Gln Pro Asp Ser
        35                  40                  45

Ile Ser His Ser Gln Ile His Gln Val Gly Ser Phe Cys Ser Leu Thr
    50                  55                  60

Pro Glu Gln Asp Val Ile Asn Ser Asn Ser His Phe Tyr Cys Glu Phe
65                  70                  75                  80

Ser Ile Lys Thr Ala Pro Phe Pro Phe His Tyr Tyr Thr Asp Gly Ile
                85                  90                  95

Lys Ala Ala Phe Val Gln Ile Asn Asp Val Glu Pro Arg Val Arg His
            100                 105                 110

Asp Val Ile Val Thr Pro Ile Ala Leu Ala Ser Pro Tyr Arg Glu Arg
        115                 120                 125

Ser Glu Ile Pro Ala Thr Asp Ala Ala Thr Leu Ser Leu Leu Pro Lys
    130                 135                 140

Pro Asn His Ile Glu Arg Leu Asp Gly Glu Phe Ala Leu Thr Ala Gly
145                 150                 155                 160

Ser Gln Ile Ser Leu Gln Ser Ser Cys Ala Glu Thr Ala Ala Thr Trp
                165                 170                 175

Leu Lys Gln Glu Leu Thr His Leu Tyr Gln Trp Gln Pro His Asp Ile
            180                 185                 190

Gly Ser Ala Asp Ile Val Leu Arg Thr Asn Pro Thr Leu Asp Glu Gly
```

|     |     |     |     |     | 195 |     |     |     |     | 200 |     |     |     |     | 205 |     |     |     |     |
|-----|-----|-----|-----|-----|-----|-----|-----|-----|-----|-----|-----|-----|-----|-----|-----|-----|-----|-----|-----|
| Ala | Tyr 210 | Leu | Leu | Ser | Val | Asp 215 | Arg | Lys | Pro | Ile | Arg 220 | Leu | Glu | Ala | Ser |
| Ser 225 | His | Ile | Gly | Phe | Val 230 | His | Ala | Ser | Ala | Thr 235 | Leu | Leu | Gln | Leu | Val 240 |
| Arg | Pro | Asp | Gly 245 | Asp | Asn | Leu | Leu | Val | Pro 250 | His | Ile | Val | Ile | Lys 255 | Asp |
| Ala | Pro | Arg | Phe 260 | Lys | Tyr | Arg | Gly | Met 265 | Met | Leu | Asp | Cys | Ala 270 | Arg | His |
| Phe | His | Pro 275 | Leu | Glu | Arg | Val | Lys 280 | Arg | Leu | Ile | Asn | Gln 285 | Leu | Ala | His |
| Tyr | Lys 290 | Phe | Asn | Thr | Phe | His 295 | Trp | His | Leu | Thr | Asp 300 | Asp | Glu | Gly | Trp |
| Arg 305 | Ile | Glu | Ile | Lys | Ser 310 | Leu | Pro | Gln | Leu | Thr 315 | Asp | Ile | Gly | Ala | Trp 320 |
| Arg | Gly | Val | Asp | Glu 325 | Val | Leu | Glu | Pro | Gln 330 | Tyr | Ser | Leu | Leu | Thr 335 | Glu |
| Lys | His | Gly | Gly 340 | Phe | Tyr | Thr | Gln | Glu 345 | Glu | Ile | Arg | Glu | Val 350 | Ile | Ala |
| Tyr | Ala 355 | Ala | Glu | Arg | Gly | Ile 360 | Thr | Val | Ile | Pro | Glu 365 | Ile | Asp | Ile | Pro |
| Gly | His 370 | Ser | Arg | Ala | Ala | Ile 375 | Lys | Ala | Leu | Pro | Glu 380 | Trp | Leu | Phe | Asp |
| Glu 385 | Asp | Asp | Gln | Ser | Gln 390 | Tyr | Arg | Ser | Ile | Gln 395 | Tyr | Tyr | Asn | Asp | Asn 400 |
| Val | Leu | Ser | Pro | Ala 405 | Leu | Pro | Gly | Thr | Tyr 410 | Arg | Phe | Leu | Asp | Cys 415 | Val |
| Leu | Glu | Glu | Val 420 | Ala | Ala | Leu | Phe | Pro 425 | Ser | His | Phe | Ile | His 430 | Ile | Gly |
| Ala | Asp | Glu 435 | Val | Pro | Asp | Gly | Val 440 | Trp | Val | Asn | Ser | Pro 445 | Lys | Cys | Gln |
| Ala | Leu 450 | Met | Ala | Glu | Glu | Gly 455 | Tyr | Thr | Asp | Ala | Lys 460 | Glu | Leu | Gln | Gly |
| His 465 | Leu | Leu | Arg | Tyr | Ala 470 | Glu | Lys | Lys | Leu | Lys 475 | Ser | Leu | Gly | Lys | Arg 480 |
| Met | Val | Gly | Trp | Glu 485 | Glu | Ala | Gln | His | Gly 490 | Asp | Lys | Val | Ser | Lys 495 | Asp |
| Thr | Val | Ile | Tyr 500 | Ser | Trp | Leu | Ser | Glu 505 | Gln | Ala | Ala | Leu | Asn 510 | Cys | Ala |
| Arg | Gln | Gly 515 | Phe | Asp | Val | Ile | Leu 520 | Gln | Pro | Gly | Gln | Phe 525 | Thr | Tyr | Leu |
| Asp | Ile 530 | Ala | Gln | Asp | Tyr | Ala 535 | Pro | Glu | Glu | Pro | Gly 540 | Val | Asp | Trp | Ala |
| Gly 545 | Val | Thr | Pro | Leu | Glu 550 | Arg | Ala | Tyr | Arg | Tyr 555 | Glu | Pro | Leu | Val | Glu 560 |
| Val | Pro | Glu | His | Asp 565 | Pro | Leu | Arg | Lys | Arg 570 | Ile | Leu | Gly | Ile | Gln 575 | Cys |
| Ala | Leu | Trp | Cys 580 | Glu | Leu | Val | Asn | Asn 585 | Gln | Asp | Arg | Met | Asp 590 | Tyr | Met |
| Ile | Tyr | Pro 595 | Arg | Leu | Thr | Ala | Leu 600 | Ala | Gly | Ser | Gly | Leu 605 | Asp | Thr | Lys |
| Ile | Pro | Ala 610 | | | | | | | | | | | | | |

( 2 ) INFORMATION FOR SEQ ID NO:5:

( i ) SEQUENCE CHARACTERISTICS:
        ( A ) LENGTH: 1713 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
GTACCCTCGA CGCCGTCCAT GCTGGTGCCG GACATGATGC CGATGTACAG TTCGCGTTCA    60
GTCATTCTGT TATCCGATTG TCATATTTCT CGTTTCCGAG GGCGAAGTCT TTAAAACTCA   120
TTGTAATTGA AAAACAAACT GAATAACCTC ATTGCTGTG  ACAAATTTTG ACAATCCACC   180
GTGATGAATG AAGGGGAAAA CATGGACCG  TTATGGCTAG ACGTTGAAGG TTGTGAACTG   240
ACGGCGGAAG ACCGCGAAAT ACTGGCGCAT CCTACCGTTG GCGGTGTCAT TTTGTTTGCT   300
CGTAACTACC ACGACAACCA ACAATTATTG GCGCTGAACA CCGCCATTCG TCAGGCGGCG   360
AAGCGCCCGA TCCTGATTGG GGTGGATCAA GAAGGTGGCC GCGTGCAGCT TTCGCGACGG   420
GTTCAGCAAG ATCCCTGCGC GCAGCTTTAT GCGCGCAGCG ACAATGGTAC GCAGTTGGCC   480
GAAGACGGCG GCTGGTTGAT GGCGGCGGAA CTCATCGCAC ACGACATTGA TCTCAGCTTT   540
GCGCCCGTAT TGGATAAGGG TTTTGATTGC CGTGCAATTG GCAACCGCGC CTTTGGTGAC   600
GATGTGCAAA CCGTGTTGAC CTATAGCAGC GCCTATATGC GCGGCATGAA ATCTGTGGGG   660
ATGGCGACCA CCGGCAAACA CTTTCCCGGT CACGGTGCGG TGATTGCCGA CTCCCATCTG   720
GAAACGCCTT ACGATGAACG TGATTCGATT GCTGACGACA TGACGATTTT CCGCGCGCAG   780
ATTGAAGCGG GCATTTTGGA TGCCATGATG CCTGCGCACG TGATTTATCC GCACTATGAT   840
GCCCAGCCCG CCAGCGGCTC TCCGTATTGG CTGAAACAGG TTTTGCGTCA GGAACTGGGC   900
TTTCAAGGCA TCGTGTTCTC GGATGATTTG AGCATGGAAG GTGCGGCGAT CATGGGCGGC   960
CCGGCAGAGC GTGCGCAGCA GTCGCTGGAT GCCGGTTGCG ACATGGTGCT GATGTGCAAC  1020
AAGCGCGAAT CGGCAGTCGC GGTGTTGGAT CAGCTACCAA TCAGTGTGGT GCCGCAAGCG  1080
CAGTCGCTGC TGAAACAGCA ACAGTTCACC TACCGTGAAC TGAAAGCGAC TGAGCGTTGG  1140
AAGCAGGCGT ATCAAGCGCT GCAGCGTTTG ATTGACGCGC ACAGCTAACG GCACATTCGC  1200
GATCAAGAAA GGCTCCCATG GGAGCCTTTT GTCAATGCAG CGATTTTGCG GCCAACGGTT  1260
AGTGGAAGCC CAATTTCTCT TTTAGTTCTT TGAGGTAACG GCGACTGACG GGACTTGAT   1320
GGCCGGAGCG GGTGATGATC TCCGCCAACC CGTTTTCCAA CAGTTTGATT TCTTTGATCG  1380
CTTTGGTGTT CACCAGATAC TGGCGATGGC AGCGCACCAA CGGCGTTTTC TCTTCCAAAA  1440
TTTTGAGCGT CAACTGGCTG GTGGCGCGTT GCTGATGGGT TTGTACGTGC ACGCCGCTGA  1500
TGTCGCTAAA CGCAAACTCC ACATCGACTG TCGGTACAAT CACAATGCGG TTCAGGCCAA  1560
TGCATGGCAC CTGATCCAGA TTATTTGGCG CTAGGGCGGA GTAGTCTTGC GTCTTGTTCA  1620
CGCTGCGCCC CAAGCGTTGG ATGGTTTTTT CCAACCTTGC CGGGTCAATC GGCTTGAGCA  1680
GGTAATCAAA CGCATTGTCT TCAAAGCCTT GCA                                1713
```

( 2 ) INFORMATION FOR SEQ ID NO:6:

( i ) SEQUENCE CHARACTERISTICS:
        ( A ) LENGTH: 328 amino acids
        ( B ) TYPE: amino acid
        ( C ) STRANDEDNESS: single
        ( D ) TOPOLOGY: linear (i i) MOLECULE TYPE: protein (x i) SEQUENCE DESCRIPTION: SEQ ID NO:6:

| Met | Gly | Pro | Leu | Trp | Leu | Asp | Val | Glu | Gly | Cys | Glu | Leu | Thr | Ala | Glu |
|---|---|---|---|---|---|---|---|---|---|---|---|---|---|---|---|
| 1 | | | | 5 | | | | | 10 | | | | | 15 | |

| Asp | Arg | Glu | Ile | Leu | Ala | His | Pro | Thr | Val | Gly | Gly | Val | Ile | Leu | Phe |
| | | | 20 | | | | 25 | | | | | 30 | | | |

| Ala | Arg | Asn | Tyr | His | Asp | Asn | Gln | Gln | Leu | Leu | Ala | Leu | Asn | Thr | Ala |
| | | 35 | | | | | 40 | | | | | 45 | | | |

| Ile | Arg | Gln | Ala | Ala | Lys | Arg | Pro | Ile | Leu | Ile | Gly | Val | Asp | Gln | Glu |
| | 50 | | | | | 55 | | | | | 60 | | | | |

| Gly | Gly | Arg | Val | Gln | Leu | Ser | Arg | Arg | Val | Gln | Gln | Asp | Pro | Cys | Ala |
| 65 | | | | | 70 | | | | | 75 | | | | | 80 |

| Gln | Leu | Tyr | Ala | Arg | Ser | Asp | Asn | Gly | Thr | Gln | Leu | Ala | Glu | Asp | Gly |
| | | | | 85 | | | | | 90 | | | | | 95 | |

| Gly | Trp | Leu | Met | Ala | Ala | Glu | Leu | Ile | Ala | His | Asp | Ile | Asp | Leu | Ser |
| | | | 100 | | | | | 105 | | | | | 110 | | |

| Phe | Ala | Pro | Val | Leu | Asp | Lys | Gly | Phe | Asp | Cys | Arg | Ala | Ile | Gly | Asn |
| | | 115 | | | | | 120 | | | | | 125 | | | |

| Arg | Ala | Phe | Gly | Asp | Asp | Val | Gln | Thr | Val | Leu | Thr | Tyr | Ser | Ser | Ala |
| 130 | | | | | 135 | | | | | 140 | | | | | |

| Tyr | Met | Arg | Gly | Met | Lys | Ser | Val | Gly | Met | Ala | Thr | Thr | Gly | Lys | His |
| 145 | | | | | 150 | | | | | 155 | | | | | 160 |

| Phe | Pro | Gly | His | Gly | Ala | Val | Ile | Ala | Asp | Ser | His | Leu | Glu | Thr | Pro |
| | | | | 165 | | | | | 170 | | | | | 175 | |

| Tyr | Asp | Glu | Arg | Asp | Ser | Ile | Ala | Asp | Met | Thr | Ile | Phe | Arg | Ala |
| | | | 180 | | | | | 185 | | | | | 190 | | |

| Gln | Ile | Glu | Ala | Gly | Ile | Leu | Asp | Ala | Met | Met | Pro | Ala | His | Val | Ile |
| | | 195 | | | | | 200 | | | | | 205 | | | |

| Tyr | Pro | His | Tyr | Asp | Ala | Gln | Pro | Ala | Ser | Gly | Ser | Pro | Tyr | Trp | Leu |
| | 210 | | | | | 215 | | | | | 220 | | | | |

| Lys | Gln | Val | Leu | Arg | Gln | Glu | Leu | Gly | Phe | Gln | Gly | Ile | Val | Phe | Ser |
| 225 | | | | | 230 | | | | | 235 | | | | | 240 |

| Asp | Asp | Leu | Ser | Met | Glu | Gly | Ala | Ala | Ile | Met | Gly | Gly | Pro | Ala | Glu |
| | | | | 245 | | | | | 250 | | | | | 255 | |

| Arg | Ala | Gln | Gln | Ser | Leu | Asp | Ala | Gly | Cys | Asp | Met | Val | Leu | Met | Cys |
| | | | 260 | | | | | 265 | | | | | 270 | | |

| Asn | Lys | Arg | Glu | Ser | Ala | Val | Ala | Val | Leu | Asp | Gln | Leu | Pro | Ile | Ser |
| | | 275 | | | | | 280 | | | | | 285 | | | |

| Val | Val | Pro | Gln | Ala | Gln | Ser | Leu | Leu | Lys | Gln | Gln | Gln | Phe | Thr | Tyr |
| | 290 | | | | | 295 | | | | | 300 | | | | |

| Arg | Glu | Leu | Lys | Ala | Thr | Glu | Arg | Trp | Lys | Gln | Ala | Tyr | Gln | Ala | Leu |
| 305 | | | | | 310 | | | | | 315 | | | | | 320 |

| Gln | Arg | Leu | Ile | Asp | Ala | His | Ser |
| | | | | 325 | | | |

(2) INFORMATION FOR SEQ ID NO:7:

(i) SEQUENCE CHARACTERISTICS:
 (A) LENGTH: 2951 base pairs
 (B) TYPE: nucleic acid
 (C) STRANDEDNESS: single
 (D) TOPOLOGY: linear (i i) MOLECULE TYPE: DNA (genomic)

(x i) SEQUENCE DESCRIPTION: SEQ ID NO:7:

```
TGTTGTCTGC GTTACCTGTC CGGTCGCGTT GCCTTTTTCG TTGTTCATAC CAATAACGAA      60
ATAAGGAAGT TCAACTATGT TCAGTCCAAA ACATTCCCTG CTGGCATTGC TGGTCGGGGG     120
GCTCTGTTCT ACCTCCGCCC TCGCTGCCGC CCCCGGCAAA CCCACCATCG GCTGGGGTGA     180
AACCAAGTTC GCCATCATCC AGGTCGATCA GGCCGCCACC TCCTACAACA AGCTGGTCAC     240
TGTCCACAAG GACGGCGCCC CGGTCAGCGT GACCTGGAAC CTCTGGTCCG GCGATGTGGG     300
CCAGACCGCC AAGGTACTGC TCGATGGCAA GGAAGTCTGG TCCGGCGCCG CCAGTGCGGC     360
GGGCACCGCC AACTTCAAGG TCACCAAGGG TGGCCGCTAT CAGATGCAGG TGGCCCTGTG     420
CAACGCCGAC GGCTGCACCC TATCCGACAA GAAGGAGATA GTGGTGGCCG ACACGGACGG     480
CAGCCACCTG GCGCCGCTCA ATGCGCCCCT GCAAGAGAAC AACAAGCCTT ACACCAACAA     540
GGCCGGCAAG GTGGTCGGGG CCTACTACGT GGAGTGGGGC GTCTATGGCC GCAAGTTCAC     600
CGTGGACAAG ATCCCGGCCA AGAACCTGAC CCACATCCTC TATGGCTTCA CCCCCATCTG     660
TGGCGGTAAC GGCATCAACG ACAGCCTGAA AGAGATCTCA GGCAGCTTCG AGGCACTGCA     720
GCGCTCCTGC GCCGGCCGTG AGGACTTCAA GGTCTCCATC CATGATCCCT GGGCCGCGGT     780
CCAGATGGGG CAGGGCAATC TCACCGCCTT CGACGAGCCC TACAAGGGCA ACTTCGGCAA     840
CCTGATGGCG CTGAAGAAAG CCAACCCAAA CCTCAAGATC CTGCCTTCCG TGGGTGGCTG     900
GACCCTGTCC GACCCCTTCT ACTTCTTCAG TGACAAGACC AAGCGCGACA CCTTCGTCGC     960
CTCCATGAAG GAGTACCTGC AGACCTGGAA ATTCTTCGAT GGCGTGGACA TCGACTGGGA    1020
GTTCCCGGGT GGCCAGGGTG CCAACCCCAA TCTGGGTGGC CCGAACGATG GCGCCACCTA    1080
TGTGGCCCTG ATGAAAGAGC TGCGCGCCAT GCTGGACGAG CTGGAAGCCG AGACCGGCCG    1140
CCAGTATGAG CTCACCTCGG CCATCAGCGC CGGCGGCGAC AAGATTGCCA AGGTGGACTA    1200
TCAGGCTGCC CAGCAGTACA TGGATTACAT CTTCCTGATG AGCTACGACT TCAGCGGCGC    1260
CTTCGATCTG AAGAACCTGG CTCACCAGAC CAACCTCTAT GCATCAAGCT GGGATCCGGC    1320
CACCAAGTAC ACCACCGACA AGGGCGTCAA GGCGCTGCTC GGCCAGGGTG TGACTCCGGG    1380
CAAGGTCGTG GTCGGTGCGG CCATGTATGG CCGTGGCTGG ACCGGGGTCA ATGGCTATCA    1440
GGCCGGCAAC CCCTTCACCG GCAGTGCGAC CGGTCCCATC AAGGGCACCT GGGAGAATGG    1500
CGTGGTGGAT TACCGCGATA TCGTCAACAA CCGCATGGGC GCGGCTGGG AGCAGGGCTA    1560
TGACGAAACG GCGGAAGCGC CTTACGTCTT CAAGGCGAGC ACCGGCGATC TCATCAGCTT    1620
CGACAACGAT CGCTCGGTCA AGGCCAAGGG GCAGTACGTG CTGGCCAACC AGCTCGGCGG    1680
CCTGTTCGCC TGGGAGATCG ATGCGGATAA CGGCGACATC TTGAACGCCA TGCACGAAGG    1740
GCTCGGCAAC GGGGACGGCG GCACCACGCC ACCGGTCAAC AAGCCGCCCG TGGCCAATGC    1800
AGGTAGCGAT CTGAGCGACA CAGGCCCGGC CGAGGTGACC CTCAACGGCG CCGCCTCCCA    1860
TGACCCCGAG AGCGGTGTGC TGAGCTACAG CTGGAAGCAG GTCTCTGGCC CGCAGGTCAG    1920
CCTGCTCGAT GCTACTCAGG CCAAGGCCCG GGTAGTGTTG ACGCCGTCA GCGCCGACAT    1980
CAACCTGGTG TTCGAGCTGA CCGTCACCGA CGATCACAAC CTCACGGCCA AGGATCAGGT    2040
GGTGGTGACC AACAAGGCGC CGCAGCCTAA CCTGCCGCCC GTAGTGACGG TACCGGCCAC    2100
CGCCAGCGTC GAATCCGGCA AGCAGGTGAC CATCAAGGCC ACCGCCTCCG ATCCGAACGG    2160
CGACGCCCTG ACCTATCAGT GGAGCCTGCC TGCGGGTCTC ACCGCCACCG GTCAGAACAG    2220
CGCGACCCTG GTAGTCACAG GCCCGAGCGT CACCAGCGAC ACCGCCTATG ACCTGAGCCT    2280
GGTGGTCACC GACGGCTCTC TGGATGCCAG TGCCGGCACC CGTCTGACCG TCAAACCGGC    2340
GAGCACTGGG GGTGGCTGTG AGGCAACCGA TCCGGATGCG GCCAACCACC CGGCCTGGAG    2400
```

-continued

```
CGCCAGCGCC GTCTACAACA CCAATGCCAA GGTGAGCCAC AAGCAGCTAG TGTGGCAAGC    2460
CAAGTATTGG ACCCAGGGCA ACGAGCCAAG CCAGACCGCG GATCAGTGGA AGCTGCTGAG    2520
TGCGGTGCAG CTCGGCTGGA ATGCCGGGGT GGCCTATAAC GCCGGCGACC TGACCAACCA    2580
CAACGGTCGC AAGTGGAAGG CCCAGTACTG GACCAAGGGT GACGAGCCCG GCAAGGCCGC    2640
CGTCTGGGTT GACCAGGGTG CTGCCAGCTG TAACTGAGTG ACATCATGAC CAAGCAATG    2700
GGGCCCGGTG CCCCATTGCT TTCTCCACCC ACCTTCCCGA CCTGCCAGAT ATTCCCAATC    2760
TGCTATCAGA ACGTCGTACA TCAGCGCTAT GCGCACCGAG GATATTTCA ATGCACCAAG     2820
ACAGCACGCA GTGGATGGGC AAACTCTCCA TCCTGGGGCT GGCGATCCTG AATATCAGCC    2880
CGCTGGCGAT GGCTCAACAG AGCAGCACGA CCGGCGAGTT TCGCAAAGAC AACAGCGCTC    2940
CCCAGATCCC C                                                         2951
```

(2) INFORMATION FOR SEQ ID NO:8:

(i) SEQUENCE CHARACTERISTICS:
        (A) LENGTH: 866 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Met Phe Ser Pro Lys His Ser Leu Leu Ala Leu Leu Val Gly Gly Leu
 1               5                  10                  15

Cys Ser Thr Ser Ala Leu Ala Ala Ala Pro Gly Lys Pro Thr Ile Gly
            20                  25                  30

Trp Gly Glu Thr Lys Phe Ala Ile Ile Gln Val Asp Gln Ala Ala Thr
        35                  40                  45

Ser Tyr Asn Lys Leu Val Thr Val His Lys Asp Gly Ala Pro Val Ser
    50                  55                  60

Val Thr Trp Asn Leu Trp Ser Gly Asp Val Gly Gln Thr Ala Lys Val
65                  70                  75                  80

Leu Leu Asp Gly Lys Glu Val Trp Ser Gly Ala Ala Ser Ala Ala Gly
                85                  90                  95

Thr Ala Asn Phe Lys Val Thr Lys Gly Gly Arg Tyr Gln Met Gln Val
            100                 105                 110

Ala Leu Cys Asn Ala Asp Gly Cys Thr Leu Ser Asp Lys Lys Glu Ile
        115                 120                 125

Val Val Ala Asp Thr Asp Gly Ser His Leu Ala Pro Leu Asn Ala Pro
    130                 135                 140

Leu Gln Glu Asn Asn Lys Pro Tyr Thr Asn Lys Ala Gly Lys Val Val
145                 150                 155                 160

Gly Ala Tyr Tyr Val Glu Trp Gly Val Tyr Gly Arg Lys Phe Thr Val
                165                 170                 175

Asp Lys Ile Pro Ala Lys Asn Leu Thr His Ile Leu Tyr Gly Phe Thr
            180                 185                 190

Pro Ile Cys Gly Gly Asn Gly Ile Asn Asp Ser Leu Lys Glu Ile Ser
        195                 200                 205

Gly Ser Phe Glu Ala Leu Gln Arg Ser Cys Ala Gly Arg Glu Asp Phe
    210                 215                 220

Lys Val Ser Ile His Asp Pro Trp Ala Ala Val Gln Met Gly Gln Gly
225                 230                 235                 240

Asn Leu Thr Ala Phe Asp Glu Pro Tyr Lys Gly Asn Phe Gly Asn Leu
                245                 250                 255
```

-continued

| | | | | | | | | | | | | | | |
|---|---|---|---|---|---|---|---|---|---|---|---|---|---|---|
|Met|Ala|Leu|Lys 260|Lys|Ala|Asn|Pro|Asn 265|Leu|Lys|Ile|Leu|Pro 270|Ser|Val|
|Gly|Gly|Trp 275|Thr|Leu|Ser|Asp|Pro 280|Phe|Tyr|Phe|Ser 285|Asp|Lys|Thr|
|Lys|Arg 290|Asp|Thr|Phe|Val|Ala 295|Ser|Met|Lys|Glu 300|Tyr|Leu|Gln|Thr|Trp|
|Lys 305|Phe|Phe|Asp|Gly|Val 310|Ala|Ile|Asp|Trp 315|Glu|Phe|Pro|Gly|Gly|Gln 320|
|Gly|Ala|Asn|Pro 325|Asn|Leu|Gly|Gly|Pro 330|Asn|Asp|Gly|Ala|Thr 335|Tyr|Val|
|Ala|Leu|Met|Lys 340|Glu|Leu|Arg|Ala|Met 345|Leu|Asp|Glu|Leu|Glu 350|Ala|Glu|
|Thr|Gly|Arg 355|Gln|Tyr|Glu|Leu|Thr 360|Ser|Ala|Ile|Ser|Ala 365|Gly|Gly|Asp|
|Lys|Ile 370|Ala|Lys|Val|Asp|Tyr 375|Gln|Ala|Ala|Gln 380|Tyr|Met|Asp|Tyr|
|Ile 385|Phe|Leu|Met|Ser|Tyr 390|Asp|Phe|Ser|Gly|Ala 395|Phe|Asp|Leu|Lys|Asn 400|
|Leu|Ala|His|Gln|Thr 405|Asn|Leu|Tyr|Ala|Ser 410|Ser|Trp|Asp|Pro|Ala 415|Thr|
|Lys|Tyr|Thr|Thr 420|Asp|Lys|Gly|Val|Lys 425|Ala|Leu|Leu|Gly|Gln 430|Gly|Val|
|Thr|Pro|Gly 435|Lys|Val|Val|Val 440|Gly|Ala|Ala|Met|Tyr 445|Gly|Arg|Gly|Trp|
|Thr|Gly 450|Val|Asn|Gly|Tyr|Gln 455|Ala|Gly|Asn|Pro|Phe 460|Thr|Gly|Ser|Ala|
|Thr 465|Gly|Pro|Ile|Lys|Gly 470|Thr|Trp|Glu|Asn|Gly 475|Val|Val|Asp|Tyr|Arg 480|
|Asp|Ile|Val|Asn|Asn 485|Arg|Met|Gly|Ala|Gly 490|Trp|Glu|Gln|Gly|Tyr 495|Asp|
|Glu|Thr|Ala|Glu 500|Ala|Pro|Tyr|Val|Phe 505|Lys|Ala|Ser|Thr|Gly 510|Asp|Leu|
|Ile|Ser|Phe 515|Asp|Asn|Asp|Arg|Ser 520|Val|Lys|Ala|Lys|Gly 525|Gln|Tyr|Val|
|Leu|Ala|Asn 530|Gln|Leu|Gly|Gly 535|Leu|Phe|Ala|Trp|Glu 540|Ile|Asp|Ala|Asp|
|Asn 545|Gly|Asp|Ile|Leu|Asn 550|Ala|Met|His|Glu|Gly 555|Leu|Gly|Asn|Gly|Asp 560|
|Gly|Gly|Thr|Thr|Pro 565|Pro|Val|Asn|Lys|Pro 570|Pro|Val|Ala|Asn|Ala 575|Gly|
|Ser|Asp|Leu|Ser 580|Asp|Thr|Gly|Pro|Ala 585|Glu|Val|Thr|Leu|Asn 590|Gly|Ala|
|Ala|Ser|His 595|Asp|Pro|Glu|Ser|Gly 600|Val|Leu|Ser|Tyr|Ser 605|Trp|Lys|Gln|
|Val|Ser|Gly 610|Pro|Gln|Val|Ser 615|Leu|Leu|Asp|Ala|Thr 620|Gln|Ala|Lys|Ala|
|Arg 625|Val|Val|Leu|Asp|Ala 630|Val|Ser|Ala|Asp|Ile 635|Asn|Leu|Val|Phe|Glu 640|
|Leu|Thr|Val|Thr|Asp 645|Asp|His|Asn|Leu|Thr 650|Ala|Lys|Asp|Gln|Val 655|Val|
|Val|Thr|Asn|Lys 660|Ala|Pro|Gln|Pro|Asn 665|Leu|Pro|Pro|Val|Val 670|Thr|Val|
|Pro|Ala|Thr|Ala|Ser|Val|Glu|Ser|Gly|Lys|Gln|Val|Thr|Ile|Lys|Ala|

|     |     |     |     |     |     | 675 |     |     |     |     |     | 680 |     |     |     |     |     | 685 |     |     |     |
|-----|-----|-----|-----|-----|-----|-----|-----|-----|-----|-----|-----|-----|-----|-----|-----|-----|-----|-----|-----|-----|-----|

```
            675                         680                         685
Thr Ala Ser Asp Pro Asn Gly Asp Ala Leu Thr Tyr Gln Trp Ser Leu
    690                 695                 700
Pro Ala Gly Leu Thr Ala Thr Gly Gln Asn Ser Ala Thr Leu Val Val
705                 710                 715                     720
Thr Gly Pro Ser Val Thr Ser Asp Thr Ala Tyr Asp Leu Ser Leu Val
                725                 730                     735
Val Thr Asp Gly Ser Leu Asp Ala Ser Ala Gly Thr Arg Leu Thr Val
            740                 745                     750
Lys Pro Ala Ser Thr Gly Gly Gly Cys Glu Ala Thr Asp Pro Asp Ala
        755                 760                 765
Ala Asn His Pro Ala Trp Ser Ala Ser Ala Val Tyr Asn Thr Asn Ala
    770                 775                 780
Lys Val Ser His Lys Gln Leu Val Trp Gln Ala Lys Tyr Trp Thr Gln
785                 790                 795                     800
Gly Asn Glu Pro Ser Gln Thr Ala Asp Gln Trp Lys Leu Leu Ser Ala
            805                 810                     815
Val Gln Leu Gly Trp Asn Ala Gly Val Ala Tyr Asn Ala Gly Asp Leu
            820                 825                     830
Thr Asn His Asn Gly Arg Lys Trp Lys Ala Gln Tyr Trp Thr Lys Gly
        835                 840                     845
Asp Glu Pro Gly Lys Ala Ala Val Trp Val Asp Gln Gly Ala Ala Ser
    850                 855                     860
Cys Asn
865
```